US011618861B2

(12) United States Patent
Javers et al.

(10) Patent No.: US 11,618,861 B2
(45) Date of Patent: Apr. 4, 2023

(54) CELLULOSIC BIOFUEL

(71) Applicant: ICM, Inc., Colwich, KS (US)

(72) Inventors: Jeremy Edward Javers, St. Joseph, MO (US); Christopher Riley William Gerken, Helena, MO (US); Charles C. Gallop, Gower, MO (US); Samuel Vander Griend, Wichita, KS (US); Jesse Spooner, Easton, MO (US); Jonathon Phillip Licklider, Cosby, MO (US); Laercio Malburg, Plate City, MO (US); Ryan Edward Hoefling, Faucett, MO (US); Douglas Bernard Rivers, St. Joseph, MO (US); Kurt A. Dieker, Wichita, KS (US)

(73) Assignee: ICM, Inc., Colwich, KS (US)

( * ) Notice: Subject to any disclaimer, the term of this patent is extended or adjusted under 35 U.S.C. 154(b) by 0 days.

(21) Appl. No.: 14/775,627

(22) PCT Filed: Mar. 14, 2014

(86) PCT No.: PCT/US2014/029042
§ 371 (c)(1),
(2) Date: Sep. 11, 2015

(87) PCT Pub. No.: WO2014/144574
PCT Pub. Date: Sep. 18, 2014

(65) Prior Publication Data
US 2016/0024406 A1 Jan. 28, 2016

Related U.S. Application Data

(60) Provisional application No. 61/799,942, filed on Mar. 15, 2013.

(51) Int. Cl.
C12P 7/14 (2006.01)
C10L 1/02 (2006.01)
C12P 7/649 (2022.01)
C08B 37/00 (2006.01)
C08H 7/00 (2011.01)
C08H 8/00 (2010.01)
C13K 1/02 (2006.01)
C12P 19/14 (2006.01)
C12P 7/10 (2006.01)
C13K 13/00 (2006.01)
B01D 3/00 (2006.01)
C13K 1/06 (2006.01)

(52) U.S. Cl.
CPC .............. *C10L 1/02* (2013.01); *B01D 3/005* (2013.01); *C08B 37/0057* (2013.01); *C08H 6/00* (2013.01); *C08H 8/00* (2013.01); *C12P 7/10* (2013.01); *C12P 7/14* (2013.01); *C12P 7/649* (2013.01); *C12P 19/14* (2013.01); *C13K 1/02* (2013.01); *C13K 1/06* (2013.01); *C13K 13/002* (2013.01); *C10L 2200/0469* (2013.01); *C10L 2290/06* (2013.01); *C10L 2290/08* (2013.01); *C10L 2290/148* (2013.01); *C10L 2290/24* (2013.01); *C10L 2290/26* (2013.01); *C10L 2290/54* (2013.01); *C10L 2290/543* (2013.01); *C10L 2290/546* (2013.01); *C12P 2201/00* (2013.01); *C12P 2203/00* (2013.01); *Y02E 50/10* (2013.01)

(58) Field of Classification Search
CPC ..... C12P 2201/00; C12P 2203/00; C12P 7/10; C12P 7/649; C13K 1/08; C13K 1/02; C10L 2290/543; C10L 2290/54; C10L 2290/26; B01D 3/005; C12K 1/06; Y02E 50/10
See application file for complete search history.

(56) References Cited

U.S. PATENT DOCUMENTS

| 4,880,473 | A |   | 11/1989 | Scott et al. |
|---|---|---|---|---|
| 5,073,201 | A | * | 12/1991 | Giesfeldt .................. A23L 7/10 127/67 |
| 5,531,385 | A | * | 7/1996 | Witsken .................... B02C 7/13 241/21 |
| 7,419,108 | B2 |   | 9/2008 | Foster |
| 7,666,637 | B2 |   | 2/2010 | Nguyen |
| 7,820,418 | B2 |   | 10/2010 | Karl et al. |
| 7,842,484 | B2 |   | 11/2010 | Lewis |

(Continued)

OTHER PUBLICATIONS

Murthy et al. Evaluation of a Dry Corn Fractionation Process for Ethanol Production With Different Hybrids; Industrial Crops and Products, vol. 29, pp. 67-72. (Year: 2009).*
Notification of International Preliminary Report on Patentability dated Sep. 24, 2015 re: PCT/US2014/029042.
Gibbons et al., Biotechnol. Bioeng. 26:1098-1107, 1984.
Taherzadeh et al., Int. J. Mol. Sci. 9:1621-1651, 2008.
Srinrinivasan et al., Cereal Chem. 84(6):563-566, 2007.
White et al., FEMS Yeast Res. 8:1175-1184, 2008.
Mosier et al., Bioresource Tech. 96:673-686, 2005.

(Continued)

*Primary Examiner* — Neil P Hammell
*Assistant Examiner* — Paul C Martin
(74) *Attorney, Agent, or Firm* — Snell & Wilmer L.L.P.

(57) ABSTRACT

This disclosure describes processes for using a single cellulosic feedstock or a combination of two or more different cellulosic feedstocks with a starch component to produce a fermented product. The process includes separating the components of the cellulosic feedstocks with fractionation, pretreating a component with wet fractionation with chemicals, hydrolysis and fermentation of the pretreated feedstock(s) to produce cellulosic biofuel. The process may include combining the cellulosic feedstock(s) with other components to a cook and/or a fermentation process, distilling and dehydrating the combined components to produce the bio fuel. The process may also include producing a whole stillage stream from the feedstock(s) and mechanically processing the whole stillage stream to produce a high-value protein animal feed.

22 Claims, 11 Drawing Sheets

(56) References Cited

U.S. PATENT DOCUMENTS

| | | | |
|---|---|---|---|
| 7,919,289 B2 | 4/2011 | Lewis | |
| 7,919,291 B2 | 4/2011 | Lewis et al. | |
| 7,968,318 B2 | 6/2011 | Lantero et al. | |
| 8,017,820 B2* | 9/2011 | Foody | C12P 7/10 162/17 |
| 8,123,864 B2 | 2/2012 | Christensen et al. | |
| 8,288,138 B2* | 10/2012 | Birkmire | C08H 8/00 203/19 |
| 8,293,504 B2 | 10/2012 | Boy et al. | |
| 2004/0187863 A1 | 9/2004 | Langhauser | |
| 2004/0234649 A1 | 11/2004 | Lewis et al. | |
| 2005/0233030 A1 | 10/2005 | Lewis et al. | |
| 2006/0057251 A1 | 3/2006 | Dawley et al. | |
| 2006/0182857 A1 | 8/2006 | Thorre | |
| 2006/0281157 A1 | 12/2006 | Chotani et al. | |
| 2007/0037267 A1 | 2/2007 | Lewis et al. | |
| 2007/0178569 A1 | 8/2007 | Leschine et al. | |
| 2008/0131947 A1 | 6/2008 | Wicking | |
| 2009/0017164 A1 | 1/2009 | Schisler et al. | |
| 2009/0029432 A1* | 1/2009 | Abbas | C12P 7/10 435/165 |
| 2009/0053800 A1* | 2/2009 | Friend | C12M 45/02 435/289.1 |
| 2009/0117635 A1* | 5/2009 | Bradley | C12P 7/06 435/165 |
| 2010/0159552 A1 | 6/2010 | Benson et al. | |
| 2010/0178675 A1 | 7/2010 | Lawton, Jr. et al. | |
| 2010/0221805 A1 | 9/2010 | Kelly et al. | |
| 2010/0227369 A1 | 9/2010 | Narendranath et al. | |
| 2010/0233771 A1 | 9/2010 | McDonald et al. | |
| 2010/0313882 A1 | 12/2010 | Dottori et al. | |
| 2011/0033896 A1 | 2/2011 | Boy et al. | |
| 2011/0053238 A1 | 3/2011 | Ohgren Gredegard et al. | |
| 2011/0070618 A1 | 3/2011 | Lewis | |
| 2011/0079219 A1 | 4/2011 | McDonald et al. | |
| 2011/0097446 A1 | 4/2011 | Ohgren Gredegard et al. | |
| 2012/0006320 A1 | 1/2012 | Nguyen | |
| 2012/0125324 A1* | 5/2012 | Fisk | A23L 1/0076 127/1 |
| 2012/0329096 A1 | 12/2012 | Foody et al. | |

OTHER PUBLICATIONS

Wright et al., Appd. Biochem. & Biotechnology, 18(1):75-90, 1988.
Devantier et al., Appd. Microbiol. & Biotechnology, 68:622-629, 2005.
Dong et al., Cereal Chem. 64(4): 327-332, 1987.
Spiehs et al., J. Anim. Sci. 80:2639-2645, 2002.
Batajoo and Shaver, Anim. Feed Sci. Tech. 71: 165-176, 1998.
Bothast et al., Appl. Microbial Biotechnol. (2005) 67: 19-25, Dec. 14, 2004.
Brekke et al., Cereal Chemistry 52(2):205-211, 1975.
Kice, Oil Mill Gazetteer p. 36-38, Jun. 1983.
PCT; International Search Report and Written Opinion dated Aug. 13, 2014 in Application No. PCT/US2014/029042.
CIPO; Office Action dated Mar. 26, 2015 in Application No. 2.846,489.

* cited by examiner

CELLULOSIC BIOFUEL

CROSS REFERENCE TO RELATED APPLICATION

This application is a U.S. National Phase and claims priority to International Application No. PCT/US2014/029042, filed on Mar. 14, 2014 which claims priority to U.S. Provisional Application No. 61/799,942 entitled "Cellulosic Biofuel" filed on Mar. 15, 2013, the respective contents of which are hereby incorporated by reference in their entirety.

TECHNICAL FIELD

The subject matter of this disclosure pertains to treating components from a single feedstock or from a combination of different feedstocks by undergoing a variety of processes that are integrated or retrofitted to an existing facility, and combining the feedstock(s) with other components produced from the existing facility to produce ethanol, cellulosic biofuel, and high-value protein animal feed.

BACKGROUND

The United States relies on imported petroleum to meet needs of transportation fuel. To reduce dependence on the imported petroleum, Congress passed Energy Policy Act to establish a Renewable Fuel Standard (RFS) Program. The RFS Program includes a mandate to blend renewable fuel into transportation fuel. The renewable fuel includes biomass-based diesel, advanced biofuel, and cellulosic biofuel. By 2022, the Environmental Protection Agency (EPA) proposed 36 billion gallons of renewable fuel to be blended under the RFS Program. For 2013, the EPA suggested that at least 10 percent of overall fuel supply used in the United States be from renewable fuel. For instance, this is an expected volume production of cellulosic biofuel at 14 million gallons annually. (EPA-420-F-13-007, January 2013).

As a result of the RFS Program, facilities are evaluating new technologies to produce cellulosic biofuel from a variety of feedstocks. Cellulosic ethanol is a biofuel produced by converting sugars in cellulose into alcohol fuel. The facilities are integrating the new technologies to produce cellulosic biofuel with their existing facilities by converting cellulosic materials and grain starches into biofuel. The integration of the new technologies to produce cellulosic biofuel with existing facilities helps lower the cost for commercial production of cellulosic biofuel by using existing piping, storage, and loading infrastructure at the existing facilities.

The cellulosic materials are abundant as cellulose is found in plants, trees, bushes, grasses, and other parts of plants (i.e., corn stovers: leaves, husks, stalks, cobs). Cellulose is a component of cell wall of green plants. However, converting cellulosic materials to cellulosic biofuel tends to be challenging. The challenges include difficulty in releasing the sugars in the cellulosic material; release of the sugars produces by-products that inhibit fermentation; and difficulty in fermenting the sugars. Accordingly, there is a need for converting cellulosic feedstock to cellulosic biofuel in a cost-efficient manner to meet the RFS mandate.

SUMMARY

This disclosure describes a process to integrate processes to an existing plant to increase overall yield. The process includes identifying an existing plant that converts grain to ethanol, wherein the existing plant comprises a milling process, a cook process, a fermentation process, a distillation process, a dehydration process, an evaporation process, a solid-liquid separation process, a propagation process. The processes to integrate include: adding a fractionation process to separate bran from other components in the feedstock, adding a pretreatment process by using water and heat to break down cellulose and hemicellulose in the bran, and adding a hydrolysis and cellulosic fermentation process to hydrolyze the bran with a cellulase enzyme and to ferment with an organism to produce cellulosic beer. Next, the process combines the cellulosic beer with starch from the grain in the existing plant into the fermentation process to increase overall yield per feedstock unit in the existing plant.

This disclosure describes a process to treat cellulosic feedstock. The process includes fractionating a cellulosic feedstock by separating components of the cellulosic feedstock into a large-particle stream from a small-particle stream, and pretreating the large-particle stream by adding water to the large-particle stream in a tank to create a low-solids slurry, wherein a percentage of solids in the low-solids slurry comprises less than about 25%. Next, the process includes injecting steam directly to the low-solids slurry to raise or to increase a temperature of the low-solids slurry, adding a chemical to the heated low-solids slurry to cause a reaction zone to occur; and hydrolyzing and fermenting the low-solids slurry to produce cellulosic beer.

This disclosure also describes a process to produce a fermented product. The process includes pretreating a cellulosic feedstock by adding heat and an acid to break down cellulose and hemicellulose and using a base for neutralization, and hydrolyzing pretreated feedstock by adding an enzyme to convert cellulose and hemicellulose to sugars and fermenting the pretreated feedstock with an organism to produce the fermented product.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Other aspects and advantages of the claimed subject matter will be apparent from the following Detailed Description of the embodiments and the accompanying figures.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items. The figures do not limit the claimed subject matter to specific embodiments described herein.

DETAILED DESCRIPTION

Overview

Figure 1:
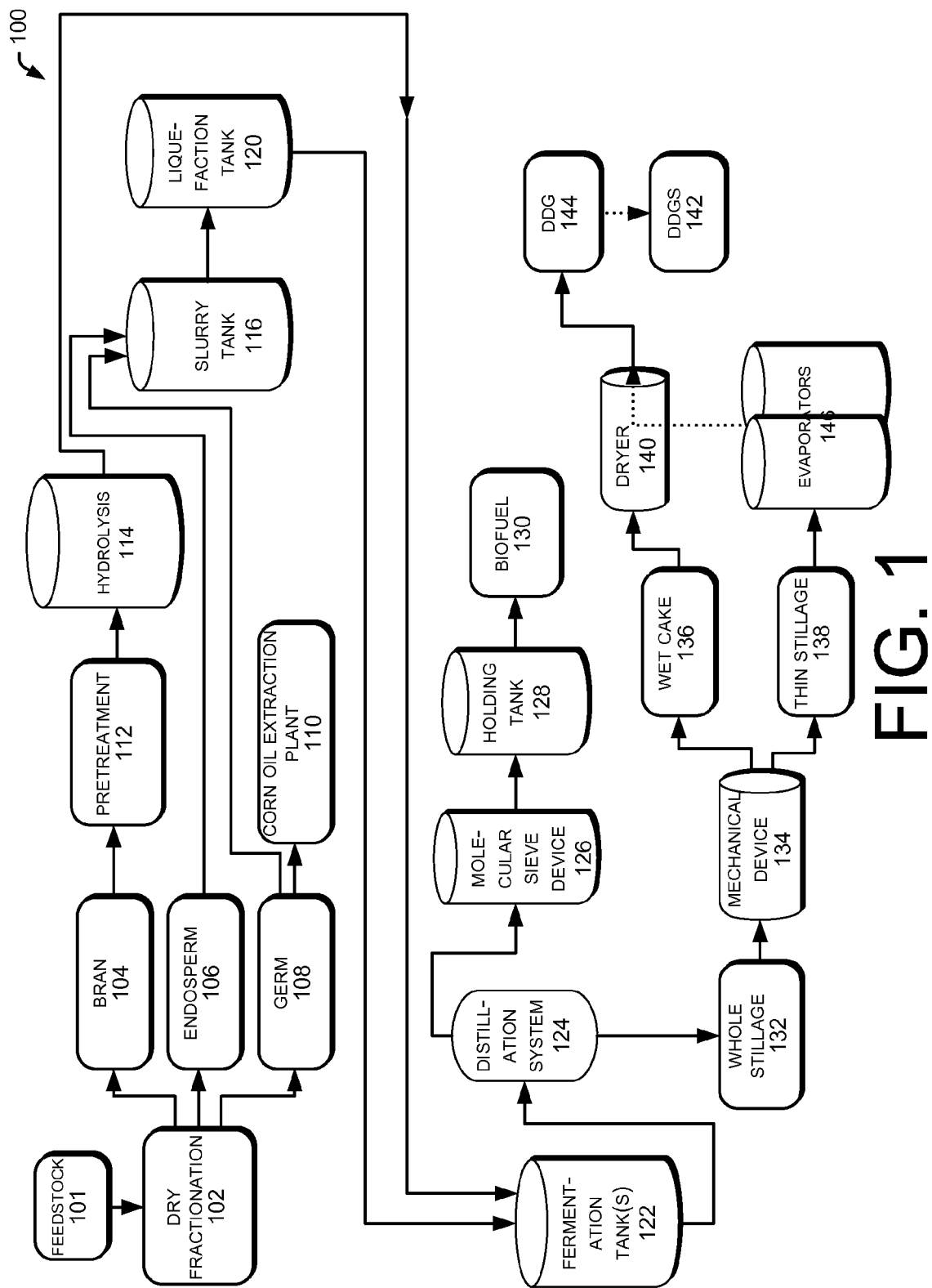
FIG. 1 illustrates an example process with dry fractionation to produce cellulosic biofuel.

This disclosure describes techniques to use a single cellulosic feedstock or a combination of two or more different cellulosic feedstocks to produce cellulosic biofuel in processes that are integrated or retrofitted with an existing facility. A benefit of producing the cellulosic biofuel includes reducing greenhouse gas emissions (GHG) by 85% over reformulated gasoline. For instance, the integrated design will decrease production costs of the existing facility while eliminating direct fossil fuel input to the existing facility. As a result, the carbon footprint may be about 42 g $CO_2e$/MJ ethanol produced. An overall expected benefit of this disclosure includes accelerating cost-effective cellulosic biofuel into the marketplace to reduce consumption of imported petroleum. Another benefit is increasing overall yield per feedstock unit in the existing plant.

Variables that affect profitability of producing the cellulosic biofuel, include being able to integrate the new technologies to lower the cost for commercial production of the cellulosic biofuel. The benefits of the integrated design include using existing roads, labor, water, piping, storage, and loading infrastructure available at the existing facility. Other benefits include generating diversified products such as heat, power, and animal feed and having decreased fouling on solid surfaces that are detrimental to the function that is part of the integrated process. In addition to these benefits, the described processes include recycling heat and power, increasing yield per feedstock unit of biofuel, and producing the cellulosic biofuel.

The integrated processes to produce the cellulosic biofuel include how to produce the fermented product by using a single cellulosic feedstock of corn and its components, a single or a combined cellulosic feedstock of grain sorghum and corn, or a combined feedstock of other portions from plants, cellulosic biomass, woody crops, energy crops, or other types of grasses. These materials are abundant as found in plants, trees, bushes, grasses, and other parts of plants (i.e., corn stovers: leaves, husks, stalks, cobs).

The integrated processes include milling or separating the components of the feedstock(s), pretreating a component of the feedstock(s) with chemicals, adjusting the pH of the pretreated feedstock(s), hydrolysis and fermentation of the pretreated feedstock(s) to produce the cellulosic biofuel. The processes may also include combining the fermented feedstock(s) with other components from the feedstock(s) for cooking and/or fermenting, distilling and dehydrating fermented feedstock(s) to produce ethanol and the cellulosic biofuel. The processes may also include producing a whole stillage stream and mechanically processing the whole stillage stream to produce a high-value protein animal feed. Any number of the described processes may be combined in any order to implement the method, or an alternate method. Moreover, it is also possible for one or more of the provided steps to be omitted.

While aspects of described techniques can be implemented in any number of different environments, and/or configurations, implementations are described in the context of the following example environment. Although the techniques are described for an integrated process, these techniques may be applied towards co-locating a plant to produce cellulosic biofuel next to an existing facility.

Illustrative Environment

FIGS. 1-11 include flow diagrams showing example processes. The processes may be performed using different environments and equipment. The equipment should not be construed as necessarily order dependent in their performance. Any number of the described processes or pieces of equipment may be combined in any order to implement the method, or an alternate method. Moreover, it is also possible for one or more of the provided steps or pieces of equipment to be omitted.

FIG. 1 illustrates an example overview process 100 with dry fractionation to produce cellulosic biofuel, ethanol, and animal feed. The series of operations may be found in a dry grind process of a facility. For instance, the process 100 shown, operates in a continuous manner. However, the cellulosic processes may be performed in a batch process, in a combined continuous and batch process, in a wet milling process, a modified dry grind process, or a dry grind process.

The process 100 may receive feedstocks that include, but are not limited to, corn stovers: leaves, husks, stalks, cobs, grain sorghum, energy sorghum, switchgrass, captive fiber, biomass, energy crops, wood crops, plants, trees, bushes, grasses, corn grain, and the like. The feedstocks may include an individual type, a combined feedstocks of two types, or any combinations or blends of feedstocks in various percentage ranges. A facility processes the cellulosic feedstocks to convert them into different co-products that may include bran to be converted to cellulosic biofuel, endosperm to be converted to starch-based and fermentation-based products such as ethanol, syrup, food, and industrial starch, germ to be extracted for oil, food grade protein, feed for high fiber animal feed, and feed grade protein meal for high protein animal feed. Other types of applications include, but are not limited to, producing chemicals, for use in other applications, and the like.

For brevity purposes, the process of using a single feedstock will be described with reference to FIG. 1. The process for a combined feedstock may be similar to the process described in FIG. 1. In an embodiment, the process 100 uses corn (i.e., stover, corn fiber) with the techniques described below to increase the yield of biofuel by about 10%. The feedstock may contain solids from about 83% to about 92%, with primary components of glucan, starch, protein, oil, and xylan.

The process 100 initially receives feedstock, 101, uses dry fractionation 102 to separate the components of the feedstock 101 into bran 104. For instance, if the feedstock 101 is corn, the components would be about 5.3% of a corn kernel, endosperm 106 which is about 82.9% of the corn kernel, and germ 108 which is about 11% of the corn kernel and about 1-3% of other components. Details of dry fractionation 102 are discussed with reference to FIGS. 2 and 3. The bran 104, which contains fiber, will be separated out from the other components, the endosperm 106, the germ 108, and additional components to be further processed with the new cellulosic technologies. The process 100 may send the germ 108 to a corn oil extraction plant 110 to process into food grade corn oil and residual germ. In another embodiment, the process 100 sends the germ 108 for further processing to a slurry tank 116.

Returning to bran 104, the process 100 sends the bran 104 for pretreatment 112 and hydrolysis 114. The pretreatment condensate may be used as cook water in the existing facility to decrease glycerol production and yeast production. The cook water may be used in the slurry tank 116. This will increase yield by about 2%. Details of the pretreatment 112 and hydrolysis 114 are discussed with reference to FIGS. 4 and 5, respectively. After the process 100 provides pretreatment 112 and hydrolysis 114 to the feedstock bran 104, this material may be referred to as hydrolysate. The hydrolysate contains fermentable sugars and compounds toxic to microorganisms. The process 100 sends the hydrolysate to the slurry tank 116. The terms bran, fiber, feedstock, and hydrolysate describe the material for processing in the integrated processes. For instance, the integrated processes may include fractionation, pretreatment 112 and hydrolysis 114 to treat the feedstock and to create hydrolysate. The processes of pretreatment 112, and hydrolysis 114 are interconnected and integrated to the existing facility. This integration helps with grain conversion capital and operating costs. The equipment for these cellulosic processes may include a pretreatment reactor, anaerobic propagator, and hydrolysis/fermentation vessels.

The process 100 may send the endosperm 106 to the slurry tank 116, to liquefaction tank 120, and to fermentation tank(s) 122. The process 100 adds water, enzymes, and the endosperm 106, with the hydrolysate into fermentation tank(s) 122. In another embodiment, the process 100 adds water, enzymes, and the endosperm 106, with the hydrolysate into the slurry tank 116 (not shown). Combining the water, enzymes, endosperm 106, and hydrolysate causes an increase yield of the starch, endosperm 106 to ethanol as well as an increased yield of the hydrolysate to cellulosic biofuel. Furthermore, the process 100 maintains a temperature between about 60 to about 100° C. in the slurry tank 116 and a residence time of about 30 to 60 minutes to convert the insoluble starch in the slurry to soluble starch. The slurry may have dissolved solids content of about 15 to 30%. Other items in the slurry tank 116 may include sugars, protein, fiber, starch, germ, grit, oil and salts, and the like as is commonly present on raw incoming grain from agricultural production. There may be one or more slurry tanks in the existing facility. In another embodiment, the process 100 further adds the germ 108 to the slurry tank 116.

In an example, the process 100 adds an enzyme, such as a low pH alpha-amylase. The low pH alpha-amylase enzyme breaks the starch polymer into short sections, termed dextrins. The process 100 adjusts the pH of the slurry to about 4 to about 5 (depending on enzyme type) in the slurry tank 116. The low pH alpha-amylase limits the amount of ammonia that enters the slurry tank 116 in order to maximize the amount of ammonia that is used to neutralize the pretreated feedstock in pretreatment 112. Additionally the low pH alpha amylase provides a viscosity break, which allows for higher solids to be utilized which in turn allows for blending of lower solids pretreated hydrolysate or beer. The low pH alpha-amylase causes rheological changes in the starch slurry, which makes it easier to pump to the tanks and for chemical balance in the process 100.

The process 100 includes cook where the slurry is heated in the slurry tank 116. Cook also includes blending the slurry with direct steam to raise the temperature to about 107° C. (225° F.) for sterilization and lowering the temperature in the flash tank to about 85° C. (185° F.). Cook also gelatinizes the starch.

The process 100 has a liquefaction tank 120 in which the slurry has a residence time of about 20 to 30 minutes. The process 100 breaks down the starch in the slurry into complex sugars called dextrins. The temperature in the liquefaction tank 120 may be about 185° F. with a pH of 5.8. The process 100 may include one or more liquefaction tanks.

In an embodiment, the process 100 adds a portion of the low pH alpha-amylase, about ⅔ in the slurry tank 116 and another ⅓ portion of the low pH alpha-amylase in a flash tank (not shown) or in the liquefaction tank 120.

Some processes may include an optional jet cooking process. When the jet cooking process is used, jet cookers (not shown) will cook the slurry. Jet cooking may occur at elevated temperatures and pressures. For example, jet cooking may be performed at a temperature of about 100 to 150° C. (about 212 to 302° F.) and at an absolute pressure of about 1.0 to 6.0 kg/cm$^2$ (about 15 to 85 lbs/in$^2$) for about five minutes. Jet cooking is a method used to gelatinize the starch.

The process 100 combines the feedstock of bran 104, which became hydrolysate and then cellulosic beer after processing, with the endosperm 106 (i.e., starch material) and/or the germ 108 in the fermentation tank(s) 122. The cellulosic beer from hydrolysis 114 is blended with the primary starch slurry stream in the fermentation tank(s) 122 for a variety of reasons. One reason for integrating the cellulosic beer with the primary starch slurry stream is that an increased yield is achieved from the primary starch fermentation as well as increased yield due to fiber conversion to ethanol. This additional increased yield is only achieved after adding the hydrolysate (i.e., cellulosic beer) to the primary starch slurry stream.

The timing for integrating the cellulosic beer with the primary starch slurry stream is critical. For instance, the process 100 has less than about 10 hours to transfer the cellulosic beer made from hydrolysis 114 to the fermentation tank(s) 122 after the primary starch slurry stream is added to the fermentation tank(s) 122. Cellulosic beer from hybrid hydrolysis and fermentation (HHF) will be discussed in detail with reference to FIG. 5, may be blended directly into the fermentation tank(s) 122 with the high solids 38% solids, corn mash during fill. This option may use a GMO yeast during HHF. The temperature of the fermentation tank(s) 122 may range from about 30° C. to about 35° C.

In another embodiment, the blending of cellulosic beer from hydrolysis 114 with the primary starch slurry stream should occur within the first 0-24 hours of the integrated starch/HHF beer fermentation. This provides the increased yield associated from the starch gallons.

At 120, the process 100 converts the slurry to mash in the liquefaction tank. This occurs at about 80 to 95° C. to hydrolyze the gelatinized starch into maltodextrins and oligosaccharides to produce a liquefied mash. Here, the mash stream has about 18 to 40% total solids content. The mash may have suspended solids content that includes fiber, germ, grit, and the like.

The process 100 may add another enzyme, such as glucoamylase in the fermentation tank(s) 122 to break down the dextrins into simple sugars. The glucoamylase breaks the short sections into individual glucose. The glucoamylase may be added at about 60° C. before fermentation, known as saccharification or at start of a fermentation process. The process 100 adjusts the pH to 5.0 or lower. In an embodiment, saccharification and fermentation may also occur simultaneously.

At 122, the process 100 adds a microorganism to the mash in the fermentation tank(s). A common species of microorganism, such as *Saccharomyces cerevisiae* may be added to convert the simple sugars (i.e., maltose and glucose) into alcohol (with solids and liquids), $CO_2$, and heat. The materials in the fermentation tank(s) 122 need to convert into beer to achieve the best yield. Within 10 hours of adding the *Saccharomyces cerevisiae*, the process 100 transfers all of the material from hydrolysis 114 to the fermentation tank(s) 122. The percent of solids is about 30% to about 50%. The process 100 maintains the temperature at about 25° C. to about 50° C.

The process 100 further uses sugars in the cook water or blend it with the high solids starch about 10 hours after inoculation. In an embodiment, separate hydrolysis and fermentation (SHF) treats the hydrolysate with a cellulase enzyme to produce a fiber hydrolysate with fermentable sugars. The process 100 transfers all of the material from hydrolysis 114 into the fermentation tank(s) 122 then adds a C5/C6 GMO yeast and *Saccharomyces cerevisiae* into the fermentation tank(s) 122, in which glucoamylase is not added yet. This converts the C5 sugars to ethanol. Once the conversion is completed, the process 100 adds the glucoamylase.

In another embodiment, the process 100 combines the bran 104, which is the pretreated feedstock with the endosperm 106, the primary slurry stream. The process 100 mixes the pretreated feedstock with the endosperm 106 of the primary slurry stream, and adds a GMO yeast to fermentation tank(s) 122 without changing parameters.

The residence time in the fermentation tank(s) 122 may be about 50 to about 100 hours. However, variables such as microorganism strain being used, rate of enzyme addition, temperature for fermentation, targeted alcohol concentration, size of tanks, and the like affect fermentation time.

The process 100 creates the alcohol, solids, and liquids in the fermentation tank(s) 122. Once completed, the mash is commonly referred to as beer, which may contain about 13 to 16% alcohol, plus soluble and insoluble solids from the grain components, microorganism metabolites, and microorganism bodies. The microorganism may be recycled in a microorganism recycling step, which is an option.

The process 100 distills the beer (which includes the cellulosic beer) to separate the alcohol from the solids and the liquids by going through a distillation system 124. The distillation system 124 may include but is not limited to a rectifier column, a beer column, a side stripper, or a distillation column. In an embodiment, the process 100 pumps the beer into a beer column, which strips the alcohol from the beer by adding heat to the bottom of the beer column from low-pressure steam from the evaporators. The material exiting from the bottom of the beer column is whole stillage 132.

The low proof alcohol leaves the top of the beer column in a vapor form and is transferred into the rectifier column. Thus, the process 100 condenses the alcohol in the distillation system 124 and the alcohol exits through a top portion of the distillation system 124 at about 90 to 95% purity, which is about 190 proof.

The bottom liquid from the rectifier column is mostly water with a small amount of alcohol. The process 100 may send the bottom liquid into a side stripper column, which strips the alcohol from the water and adds it back into the rectifier column. This stream may be used as cook water in pretreatment 112 or in the slurry tank 116.

At 126, the process 100 removes moisture from the 190 proof alcohol by going through a molecular sieve device. The molecular sieve device 126 includes one or more dehydration column(s) packed with molecular sieves to yield a product of nearly 100% alcohol, which is 200 proof.

The process 100 adds a denaturant to the alcohol prior to or in the holding tank 128. Thus, the alcohol is not meant for drinking, but is to be used for motor fuel purposes. At 130, an example product that may be produced is biofuel, to be used as fuel or fuel additive for motor fuel purposes. The biofuel 130 includes ethanol produced from the starch fermentation process as well as cellulosic biofuel produced from the integrated processes of pretreatment 112 and hydrolysis 114.

Returning to 132, the water rich product remaining from the distillation system 124 is commonly referred to as whole stillage. The components in the whole stillage 132 may include suspended grain solids, materials, and water. For instance, this material includes fat, protein, fiber, and minerals. Whole stillage 132 falls to the bottom of the distillation system 124 and passes through a mechanical device 134. The mechanical device 134 separates the whole stillage 132 to produce wet cake 136 and thin stillage 138. The mechanical device may include a centrifuge or any other type of separation device.

The wet cake 136, composed primarily of solids, may be referred to as Wet Distillers Grain (WDG). The process 100 may transfer some of the wet cake 136 to one or more dryer(s) 140 to remove moisture. This drying produces low-protein animal feed, Dried Distillers Grain (DDG) 144, which may be stored in tanks (not shown). Liquid that has been separated and concentrated is syrup. The dried syrup is added back into the DDG 144 to create Dried Distillers Grain with Solubles (DDGS) 142. The DDGS 142 has almost an indefinite shelf life and may be shipped to any market for feed to livestock.

The color of the DDGS 142 has become a quality factor for some buyers in export markets. The color of the DDGS 142 may be used to differentiate quality, whether real or perceived and affects value. The color of the DDGS 142 is a subjective evaluation based on a five-color score card and/or Hunter or Minolta colorimeters. The light-colored DDGS may generate a significant price premium. In an embodiment, the process 100 blends the DDGS with corn stover or other suitable materials without affecting the nutritional quality of the feed ingredients.

Returning to 134, the mechanical device 134 produces thin stillage 138. A stream of the thin stillage 138 is sent to the evaporators 146 to boil away water, leaving a thick syrup (i.e., 25 to 40% dry solids) that contains soluble (dissolved), fine suspended (generally less than 50 μm) and buoyant suspended solids from fermentation. As mentioned above, the process 100 adds some of the syrup into the DDG 144, shown in dotted lines, to create DDGS 142. In an embodiment, the process 100 sends the water condensed from the evaporators 146 to be used as cook water or as pretreatment water. In another embodiment, a methanator treats the evaporator condensate to be reused as process water. The methanator also treats biogas, which is sent to the dryer 140.

The thick syrup from evaporators 146 may be sent to the dryer 140 with the wet cake 136 (i.e., WDG) to produce DDGS 142. In an embodiment, the thick syrup from the evaporators 146 may be sold separately.

Dry Fractionation Process

Figure 2:
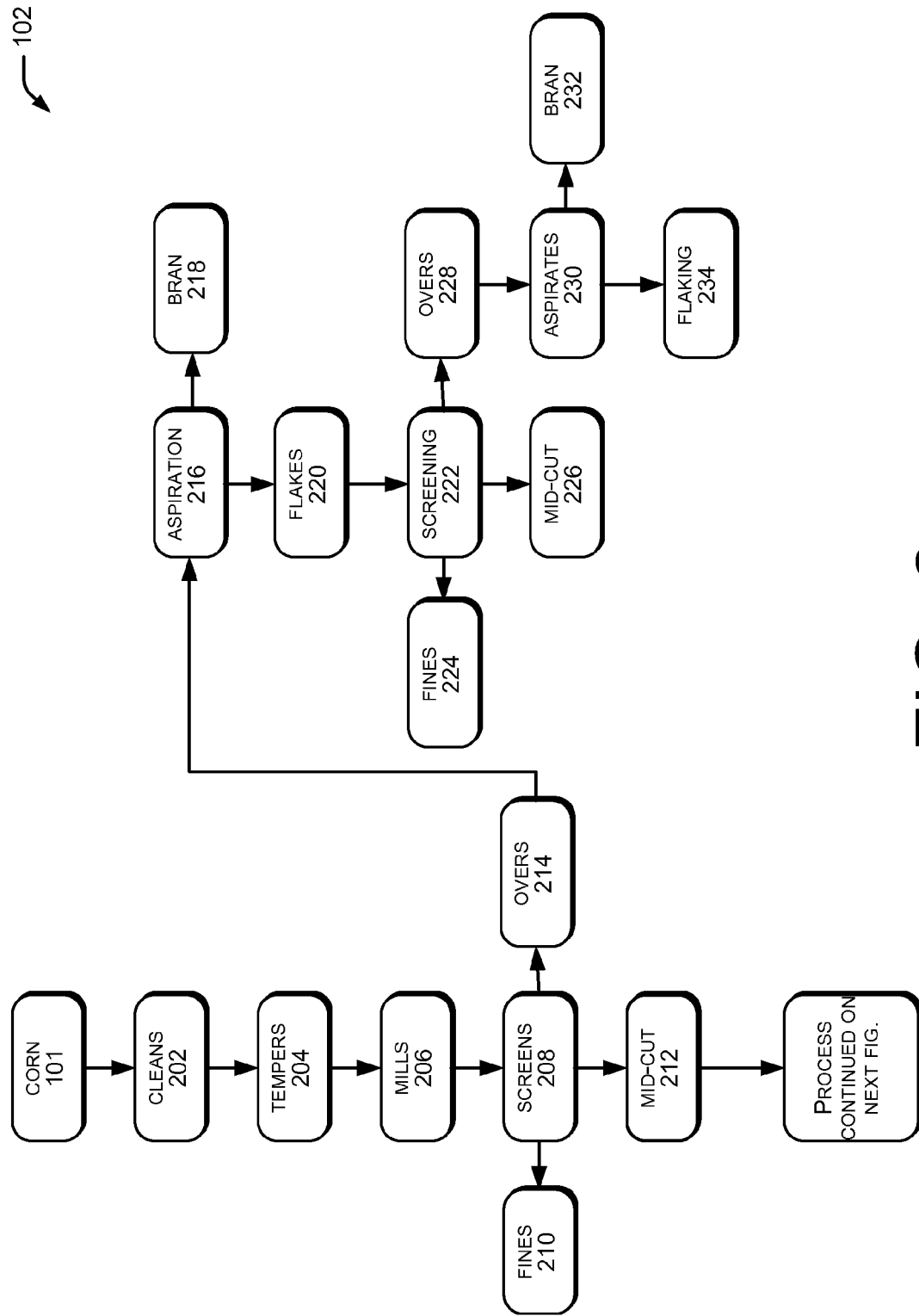
FIGS. 2 and 3 illustrate an example process of dry fractionation.
Figure 3:
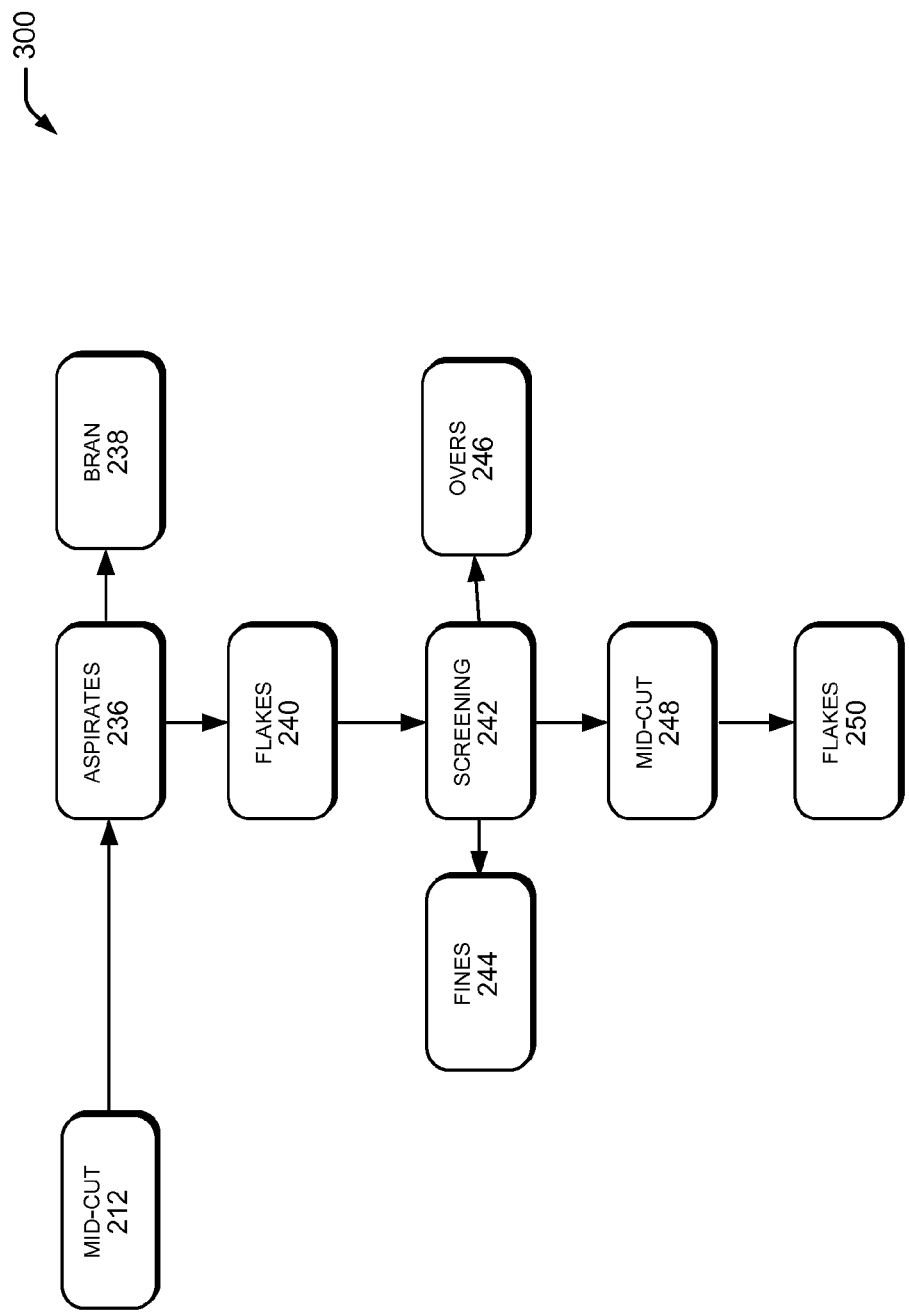

FIGS. 2 and 3 illustrate an example process of dry fractionation (DF) 102. DF 102 uses a variety of milling and separation processes to break the corn kernel into fractions of bran 104, endosperm 106, and germ 108. The DF 102 is a 3-stage grind and separation process. Any stages or combinations may be used. Devices to mill or grind the corn 101 include but are not limited to, a hammer mill, roller mill, disc mill, ball mill, pin mill, a shaker table, an aspiration system, and the like. The DF 102 increases plant efficiency, lowers greenhouse gas emissions, and produces co-products of higher value.

In FIG. 2, the DF 102 receives corn 101 as feedstock, cleans 202, and tempers 204 the feedstock. With the feedstock degerminated, the process 102 mills 206 the feedstock through a roller mill. After the feedstock has been milled 206, the process 102 screens 208 the milled feedstock into multiple grades by particle sizes, such as fines 210, mid-cut 212, and overs 214. Discussion of the mid-cut 212 continues with reference to FIG. 3.

Continuing at the overs 214, the process 102 sends the overs 214 for aspiration 216 and produces bran 218. The DF 102 flakes 220 some of the overs 214 from aspiration 216 before screening 222 the milled feedstock into multiple grades by particle sizes, such as fines 224, mid-cut 226, and overs 228. The DF 102 again aspirates 230 the overs 228 into bran 232 and continues with flaking 234. Flaking 234 rolls out uncrushed small-grain or pre-crushed seeds to form flakes for oil extraction.

In FIG. 3, the DF 300 continues the process from the mid-cut 212 from FIG. 2. The DF 300 aspirates 236 the mid-cut 212 and produces bran 238. The DF 300 flakes 240 some of the mid-cut 212 from aspiration 236 before screening 242 the milled feedstock into multiple grades by particle sizes, such as into fines 244, mid-cut 248, and overs 246. The process 300 flakes 250 the mid-cut 248. As discussed above, flaking 250 rolls out uncrushed small-grain or pre-crushed seeds to form flakes for oil extraction.

The bran 218, 232, and 238 fractionated may be portions of the bran 104 sent to pretreatment 112 in the process 100. The bran 104 may range from about 83% to about 92% solids, when received into the process 100. The components in the bran 104 may include but are not limited to glucan, starch, and xylan. A glucan molecule is a polysaccharide of D-glucose monomers, linked by glycosidic bonds. Glucans include but are not limited to glycogen, dextran, starch, cellulose, and the like. Xylan is a type of highly complex polysaccharides found in plant cell walls. Xylans are polysaccharides made from units of xylose (a pentose sugar). Xylans are almost as ubiquitous as cellulose in plant cell walls and contain predominantly β-D-xylose units linked as in cellulose.

Pretreatment of the Feedstock

Figure 4:
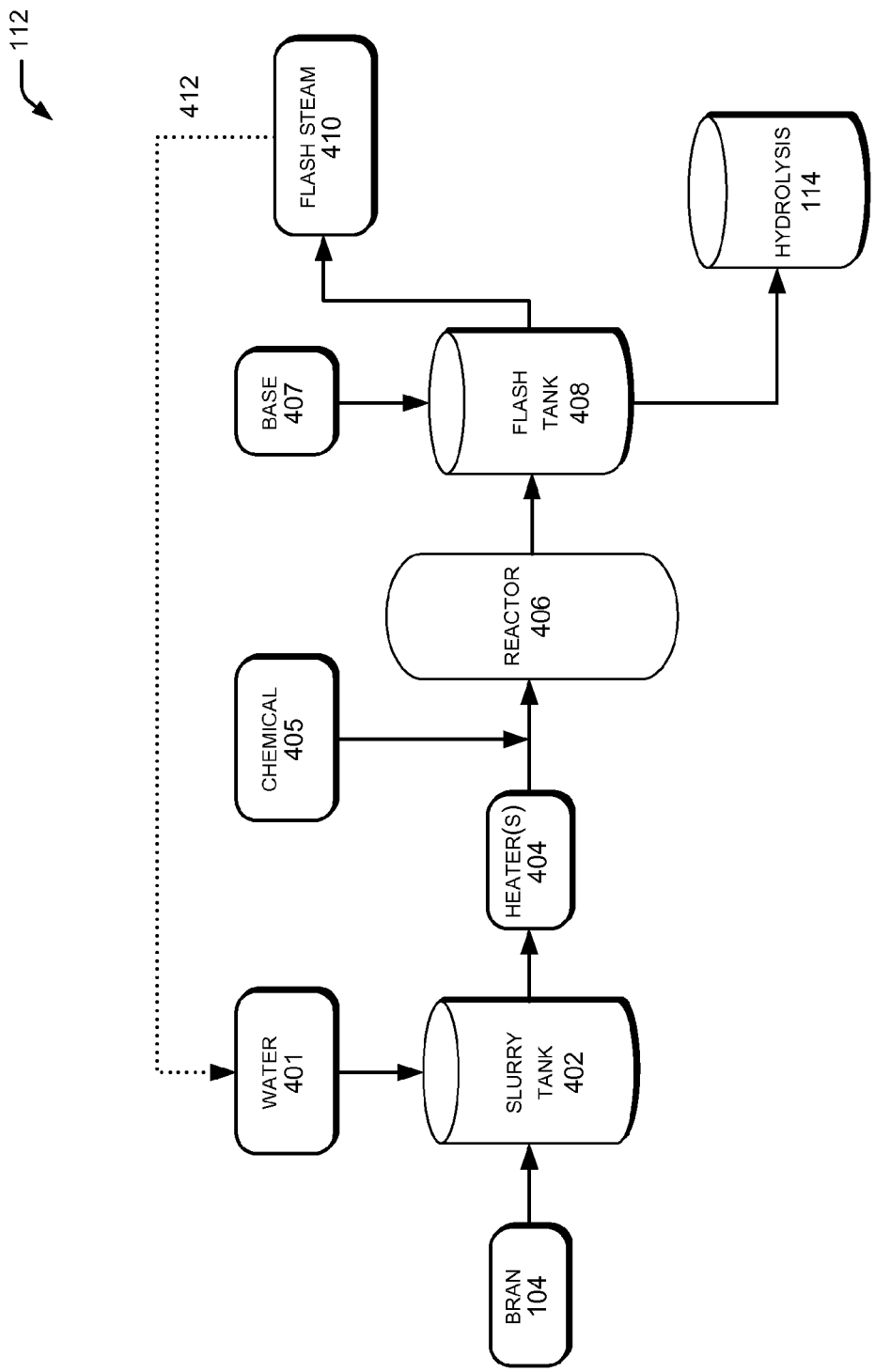
FIG. 4 illustrates an example process of pretreatment.

FIG. 4 illustrates an example process of pretreatment 112. The bran 104 is cellulosic feedstock, which is composed mostly of cellulose, hemicellulose, and a small amount of lignin. Cellulose and hemicellulose can be converted by enzymes to sugars and then fermented to a product. The use of cellulosic feedstock requires pretreatment 112 to open the fiber so enzymes may access the cellulose and hemicellulose. However, the acid degradation of hemicellulose gives off furfural.

Pretreatment 112 breaks down the structure of the cellulosic feedstock. The cellulose and hemicellulose are primary sources of sugar in the cellulosic feedstock. The pretreatment 112 uses a chemical combined with high temperatures and pressure to break down the cellulose and hemicellulose. Pretreatment 112 converts majority of the cellulose and hemicellulose to sugars.

In FIG. 4, the pretreatment 112 adds water 401 to wet the bran 104 in a slurry tank 402. The temperature of water may range from about 82° C. to about 205° C. (about 180° F. to about 400° F., about 355 K to about 478 K). The slurry tank 402 may include an agitator with upflow or downflow, which agitates a low-solids slurry stream of the bran 104 with the heated water. The low-solids slurry is about 10% to about 30% total solids. In other embodiments, the low-solids slurry is about 10% to about 20% total solids, or the low-solids slurry is about 10% to about 25% total solids. The pretreatment 112 may use evaporator condensate as the source of water in the slurry tank 402, which has a low pH. For instance, the evaporator condensate may be retrieved from the existing facility's evaporators 146. The condensate retrieved from the evaporator 146 has acetic acid, which makes the pretreatment 112 more efficient and improves the quality of the pretreatment 112.

In another embodiment, the first effect steam recycles a portion of pretreatment condensate directly to a pretreatment water tank (not shown). In yet another embodiment, the water 401 for the slurry tank 402 comes from steam of flash tank condensate and/or steam from existing facility and side stripper bottoms. In another embodiment, some of the pretreatment condensate from the pretreatment 112 may be recycled to the existing facility. It is possible to use pretreatment condensate as cook water in the existing facility to decrease glycerol production and yeast production. This will cause an increase in yield of 2%. Currently, the process 100 may send this through the methanator to get rid of furfural and acetic acid generated from the pretreatment process. However, there is actual value in using pretreatment condensate as cook water.

The pretreatment 112 adds the heated water 401 to the bran 104 to create the low-solids slurry in the slurry tank 402 to a temperature range of about 82° C. to about 104° C. (about 180° F. to about 220° F.). The low-solids slurry has a residence time of about 1 minute to about 12 minutes in the slurry tank 402 with a pH of less than 4. The residence time varies depending on the size of the slurry tank 402, the percentages of solids, the temperature of the materials and such.

The pretreatment 112 injects direct steam to the low-solids slurry stream. The direct steam occurs through heater(s) 404. The heater may include one to about six heaters that may operate in a series or in parallel. Here, the heater(s) 404 may add steam directly to the low-solids slurry stream past atmospheric temperature. For instance, the temperature reached is greater than about 100° C. (about above 212° F.), above boiling. This occurs for about few seconds to about few minutes depending on the flow rate of the stream and the number of heaters being utilized in the pretreatment 112.

In an embodiment, the pretreatment 112 injects a chemical 405, such as an inorganic acid to cause a reaction zone to occur. This is possible due to the amount of low solids in the low-solids slurry stream. The reaction zone occurs from after a final heater to a flash tank.

The chemical 405, inorganic acid, may include but is not limited to sulfuric, phosphoric, and nitric acid. The concentration may be used at 1-5% of the acid as dry weight of the fiber. For example, in an embodiment, the pretreatment 112 uses sulfuric acid at 2-4% w/w of the dry solids of the bran 104. The pH is less than 2 for the low-solids slurry stream that has been injected with the chemical 405, the inorganic acid.

In an embodiment, the pretreatment 112 heats the low-solids slurry stream through a series of two heaters 404 to temperatures greater than about 100° C. (about above 212° F.). The pretreatment 112 injects sulfuric acid into the low-solids slurry stream, and then heats the low-solids slurry stream with injected sulfuric acid through a third heater to temperatures that are greater than about 143° C. (about 290° F.).

Next, the pretreatment 112 sends the low-solids slurry stream to a reactor 406. The reactor 406 may include an agitator with upflow, radial or downflow, which agitates the low-solids slurry stream. The process in the reactor 406 hydrolyzes the cellulose and hemicellulose. The high temperature water may separate the materials in the low-solids slurry stream. This occurs in the reactor 406 with a residence time of about 6 minutes to about 14 minutes as the optimal range and about 154° C. to about 188° C. (about 310° F. to about 370° F.) as the optimal temperature range. The pressure is controlled at saturated steam pressure in the slurry tank 402, plus 10-100 psig.

The pretreatment 112 sends the pretreated feedstock from the reactor 406 to a flash tank 408. The reactor 406 releases the pretreated feedstock with an explosive decompression. The flash tank 408 may include an agitator with upflow or downflow, which agitates the pretreated feedstock.

In an embodiment, the pretreatment 112 further adjusts the pH of the pretreated feedstock by neutralizing it with a base 407 in the flash tank 408. The base 407 that may be used includes, but is not limited to, anhydrous ammonia, sodium hydroxide, potassium hydroxide, calcium hydroxide, calcium oxide, waste caustic, aqua ammonia, or any other bases. The amount of base 407 may range from 19% to 30% weight. The calculations for the amount of base 407 are based on a mass balance to adjust the pH for the integrated process/beer fermentations. Based on this, urea used in the existing facility will be replaced by base 407 without having to inject the base 407 directly into a fermentation tank. Thus, a majority of nitrogen may be obtained that is needed for fermentation in the existing facility by supplying it with the pretreated material.

Next, the pretreated feedstock undergoes hydrolysate conditioning. This occurs by adding more base to the pretreated feedstock, now referred to as hydrolysate, until the base requirement is satisfied for fermentation. In an embodiment, the pretreatment 112 further completes adjusting the pH of liquid portion of the hydrolysate to about 4 to about 6 with another base.

The base 407 that may be used, but is not limited to, includes anhydrous ammonia, sodium hydroxide, potassium hydroxide, calcium hydroxide, or any other bases. The pretreatment 112 adjusts the temperature of the hydrolysate to about 40° C. to 60° C. (about 104° F. to about 140° F.) in the flash tank 408. The pressure is −10 to 10 psig.

In an embodiment, the pretreatment 112 adds anhydrous ammonia to adjust the pH to greater than 4.5 and in quantities sufficient to supply the fermentations in the existing facility. The pretreatment 112 further adds additional ammonia to the hydrolysate until the ammonia requirement is satisfied, then adds sodium hydroxide to the hydrolysate for completing the pH adjustment.

The flash tank 408 provides flash steam 410 and the hydrolysate to be further processed in hydrolysis 114. In an embodiment, the water 401, may come from the flash steam 410 given off by the flash tank 408 in the pretreatment 112. This is shown by a dotted line 412 from flash steam 410 to water 401.

In another embodiment, the process 100 takes the pretreated material, hydrolysate, from pretreatment directly to the existing facility. The embodiment sends the hydrolysate directly to the slurry tank 116 or adds the hydrolysate directly to the fermentation tank(s) 122 without going through the hydrolysis processes.

Examples of data are illustrated in tables towards the end of the description. The pretreatment 112 data show the percentage of solids, percentage of acids used, percentage of different bases used, percentages of mixed bases used, and temperatures during the process. Factors that affect pretreatment and hydrolysis include amount of cellulose, cellulose crystallinity, available surface area, amount and nature of lignin, type and amount of hemicellulose.

Hydrolysis of Hydrolysate

Figure 5:
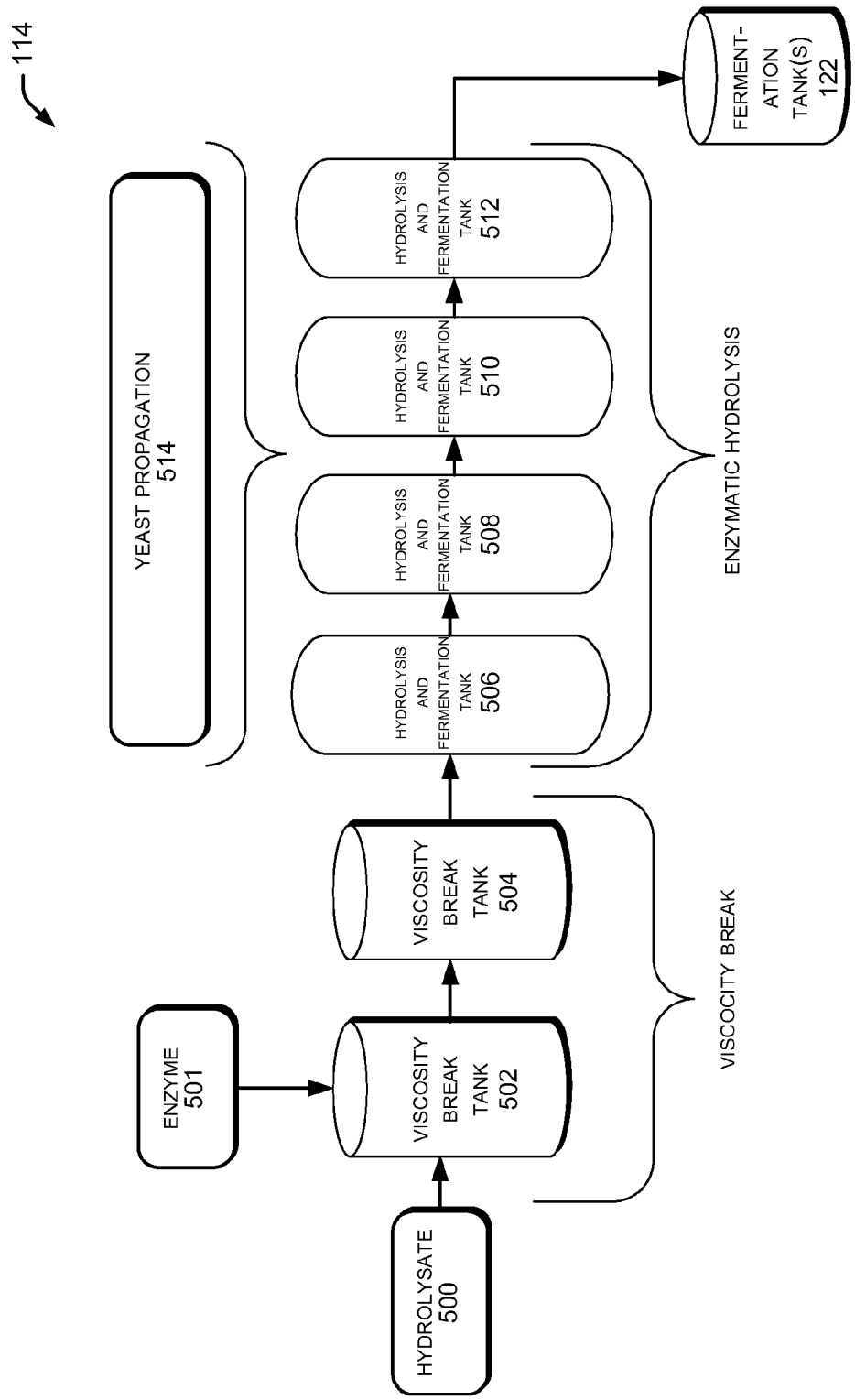
FIG. 5 illustrates an example process of hydrolysis.

FIG. 5 illustrates an example process of hydrolysis. As mentioned, this may be in a batch or a continuous process. Hydrolysis 114 converts the hydrolysate, e.g., the pretreated bran 104, most of the cellulose and remaining post-pretreatment hemicellulose to glucose and xylose with a cellulase enzyme. This integrates the processes of pretreatment 112, and hydrolysis 114 with the processes of the existing facility.

In FIG. 5, an embodiment of hydrolysis 114 is hybrid hydrolysis and fermentation (HHF) of cellulose, which maximizes yield increase. HHF process may begin with a separate hydrolysis step and ends with simultaneous hydrolysis and fermentation. The HHF process receives the hydrolysate 500 from the flash tank 408 of pretreatment 112 into a first viscosity break tank 502. The pretreatment 112 opened the fibers to increase enzyme accessibility while minimizing glucose loss. Next, the HHF process adds the enzyme 501, such as a cellulase enzyme to the hydrolysate 500 in the first viscosity break tank 502. There may be zero or more viscosity break tanks depending on variables, such as capacity of the integration processes, the percentage of solids, the size of the tanks, and such. The viscosity break tanks 502, 504 may include an agitator with upflow or downflow, which agitates the hydrolysate 500.

In an embodiment, there may be zero viscosity break tanks. In yet another embodiment, there may be one viscosity break tank. In yet another embodiment, there may be more than two viscosity break tanks.

Converting cellobiose to glucose by β-glucosidases is a key factor for reducing cellobiose inhibition and enhancing the efficiency of cellulase enzymes for producing cellulosic biofuel. Cellobiose is a watersoluble disaccharide with two glucose molecules linked by β(1,4) bonds, which is obtained by breakdown of cellulose upon hydrolysis. β-glucosidase is a glucosidase enzyme which acts upon β1,4 bonds linking two glucose or glucose-substituted molecules, such as cellobiose.

The five general classes of cellulase enzymes include endoglucanse, cellobiohydrolase, cellobiase, oxidative cellulases, and cellulose phosphorylases. Beta-1,4-endoglucanase is a specific enzyme that catalyzes the hydrolysis of cellulose. β-glucosidase is an exocellulase with specificity for a variety of beta-D-glycoside substrates. It catalyzes the hydrolysis of terminal non-reducing residues in beta-D-glucosides with release of glucose. The cellulase enzyme may include, but is not limited to, CTec2, CTec3, CodeXyme® 4 and CodeXyme® 4X, ACCELLERASE® TRIO™, and the like.

In an embodiment, hydrolysis 114 uses CTec2, a complex cocktail cellulase enzyme available from Novozymes that degrades the cellulose to fermentable sugars. It includes a blend of aggressive cellulases, a high level of β-glucosidases, and hemicellulase. CTec2 offers a high conversion yield that is inhibitor tolerant. CTec2 has lower operating costs while increasing process flexibility.

In another embodiment, hydrolysis 114 uses CTec3, a cellulase and hemicellulase complex enzyme available from Novozymes that degrades the cellulose and hemicellulose to fermentable sugars. It includes a blend of cellulase of advanced GH61 compounds, improved β-glucosidases, and hemicellulase. CTec3 is a cost-efficient solution, since less enzyme will be needed for conversion.

The HHF process carries out hydrolysis of the hydrolysate 500 in the temperature range of about 40° C. to about 60° C. and adjusts the pH of the hydrolysate 500 to about 4.2 to 6 in the first viscosity break tank 502. In embodiments, the HHF process may add base to any of the viscosity break tanks. The HHF process occurs for about 12 to about 33 hours to achieve a target enzymatic conversion of glucan to glucose and xylan to xylose. In an embodiment, the enzymatic conversion may be greater than 50%. In another embodiment, the enzymatic conversion may be greater than about 90%.

Hydrolysis 114 requires an organism capable of metabolizing both 5-carbon and 6-carbon sugars present in the hydrolysate 500. A genetically modified or metabolically engineered organism may provide the most robust candidate, capable of fermenting both the 6-carbon sugars typically encountered in traditional corn ethanol processing as well as the 5-carbon sugars resulting from the degradation of the cellulosic feedstocks. Both the overexpression of native traits and the addition of new traits may be required to arrive at a yeast strain capable of efficiently utilizing the sugars present in the hydrolysate 500. The genetic modification of yeasts and other microorganisms is well studied and a suitable organism may be obtained from a number of suppliers who specialize in providing commercial quantities of yeast to the fuel and beverage production industries. The yeast may include, but is not limited to, a C5/C6 Genetically Modified Organism (GMO) yeast, a *Saccharomyces cerevisiae* (*S. cerevisiae*) yeast, and such. The C5/C6 GMO is a genetically modified *Saccharomyces cerevisiae* (*S. cerevisiae*). In another embodiment, hydrolysis 114 uses a bacteria to metabolize the 5-carbon and 6-carbon sugars in the hydrolysate.

In an embodiment, the HHF process lowers the temperature of the hydrolysate 500 to about 20° C. to about 45° C. (about 68° F. to about 113° F.) in the second viscosity break tank 504 to add yeast. The lower temperatures are needed for the yeast and to facilitate fermentation. The HHF process adjusts the pH of the hydrolysate 500 to about 4.5 to 5.2 in the second viscosity break tank 504. In an embodiment, the HHF process adds CTec2 into the first viscosity break tank and adds a C5/C6 Genetically Modified Organism (GMO) yeast into the second viscosity break tank 504. The HHF process may use a range of percentages for the C5/C6 GMO propagate, such as about 4% to about 11% of HHF volume.

This allows the C5/C6 GMO yeast to convert both C5 and C6 sugars to cellulosic biofuel over an additional 25 to 50 hours while enzymatic hydrolysis of cellulose proceeds at a lower rate relative to hydrolysis at 50° C. (i.e., simultaneous saccharification and fermentation (SSF)).

After the viscosity breaks, the material goes through hydrolysis tanks. The number of hydrolysis tanks may range from one to six tanks. In an embodiment, there are four hydrolysis and fermentation tanks 506, 508, 510, 512. The HHF process lowers the temperature range of the hydrolysate 500 to about 30° C. to about 35° C. (120° F. to about 140° F.) and adds base to optimize the pH in the range of 4 to 5.5 in the hybrid hydrolysis and fermentation tanks 506-512. The solids being processed in 116, 120 have about 30% to 44% (w/w) to maintain the desired ethanol titer in the final beer. The HHF process produces more than 9% increase in yield per bushel. The HHF process produces a low titer beer (35-50 g/L ethanol), which may be blended into the fermentation tanks(s) 122 of the existing facility as shown in FIGS. 5 and 1.

In an embodiment, the HHF process may include no viscosity tanks and four hydrolysis and fermentation tanks. The material from pretreatment goes directly into the hydrolysis tanks and held at about 45° C. to about 55° C. The temperature is lowered in the hydrolysis tank and yeast is added to the material. In an embodiment, the HHF process may include one viscosity tanks and four hydrolysis and fermentation tanks. In yet another embodiment, the HHF process may include the two viscosity break tanks, three hydrolysis and fermentation tanks, and one surge tank. This configuration reduces capital costs by reducing the amount of equipment needed. For instance, this embodiment includes the process steps as described above but the surge tank reduces the number of hours needed for fermentation. The residence time for fermentation may occur for about 10 hours to about 75 hours, which reduces the fermentation time as previously described. In yet another embodiment, the HHF process is similar to the processes described but the fermentation time is less than about 60 hours with the three hydrolysis tanks and one surge tank.

In yet another embodiment, the HHF process performs similar steps in the first and the second viscosity break tanks. However, the HHF process starts the temperature of the hydrolysate at about 30° C. to about 35° C. and adds a cellulase enzyme in the first viscosity-break tank. Then the HHF process adds a yeast into the second viscosity break tank. In the embodiment without the second viscosity break tank, the HHF process adds the yeast in the hydrolysis and fermentation tank. This ferments for about 24 hours. Then, the HHF process increases the temperature of the hydrolysate to about 45° C. to about 60° C. so the enzymes may convert cellulose to glucose. The cellulosic beer goes to the fermentation tank(s) 122.

In another embodiment, the hydrolysis 114 may be separate hydrolysis and fermentation (SHF), which starts with the temperature of the hydrolysate at about 45° C. to about 55° C., adds a cellulase enzyme, with a residence time of 3 to 5 days to achieve a target enzymatic conversion of glucan to glucose (i.e., >90% conversion). This step produces a hydrolysate containing fermentable sugars, which is then introduced into a slurry tank 116 of the existing facility. In this embodiment, the C5 sugars are not fermented and the integrated process displaces the cook water with the hydrolysate to the existing facility. This option improves average yield by about 7%. With this embodiment, another option is to time the addition of the glucoamylase in about 72 hours after the start of fill occurs. In another option, a GMO yeast is added in fermentation and the glucoamylase is added after xylose is fermented.

In yet another embodiment, the hydrolysis 114 may be simultaneous saccharification and fermentation (SSF), which starts by receiving the hydrolysate from pretreatment 112 and sets the temperature of the hydrolysate to about 45° C. to about 55° C. SSF adds a cellulase enzyme into the hydrolysate until there is 90% of the cellulose converted to sugars. Next, the SSF process adds a yeast for fermentation. The cellulosic beer is sent to the fermentation tank(s) 122.

In another embodiment, the SSF process starts by receiving the hydrolysate from pretreatment 112 and decreases the temperature of the hydrolysate to about 30° C. to about 35° C. as described above for the second viscosity break tank. Here, the SSF process adds a cellulase enzyme into the hydrolysate with the decreased temperature. Next, the SSF process adds a yeast for fermentation. The cellulosic beer is sent to the fermentation tank(s) 122.

In yet another embodiment, the SSF process starts with the temperature of the hydrolysate to about 30° C. to about 35° C. and adds a cellulase enzyme. Next, the SSF process adds a yeast, which allows fermentation of xylose to occur in about 24 hours, and increases the temperature to about 50° C. to about 60° C. so the enzyme can convert glucan to glucose. The cellulosic beer may be sent to the fermentation tank(s) 122 of the existing facility.

Examples of data are illustrated in tables towards the end of the description. The hydrolysis 114 data show the percent conversions for glucose and xylose, hydrolysis time and total HHF time, and the different types of hydrolysis tested.

C5/C6 Yeast Propagation

In FIG. 5, the yeast propagation 514 is a process to increase cell number by reproduction. The yeast may be supplied in various forms, such as cream, liquid, compressed, and active dry yeast (ADY). The yeast propagation 514 may start with a liquid yeast, a cream yeast, a compressed yeast, or an ADY.

This may be an aerobic propagation where the yeast is inoculated into a suitable fermentable medium in tank(s). In embodiments, the process may add hydrolysate 500 and/or may add components from liquefaction to the yeast propagation 514. The propagation process controls and monitors factors, such as temperature, nutrient additions, substrate concentrations, and amount of oxygen, to ensure growth inside the tank(s). Suppliers of yeast provide instructions on storage, inoculation, fermentable medium, etc.

The yeast propagation 514 is a C5/C6 GMO microaerophillic propagation on mixtures of corn mash (i.e., about 20-35% solids) and corn fiber hydrolysate (i.e., about 10-20% solids) are carried out for 12-24 hours prior to inoculation into the hydrolysis and fermentation tanks 506 508, 510, 512 as described above. In an embodiment, the process 100 delivers the yeast for propagation to the integrated design facility in a same manner as to existing facility today (i.e., as Active Dry Yeast or as liquid). The variables for the propagation of the C5/C6 GMO yeast are a temperature range of about 30° C. to about 35° C. and pH in the range 4 to 5.5 pH with a natural swing.

Cellulosic Process with Front-End Wet Fractionation

Figure 6:
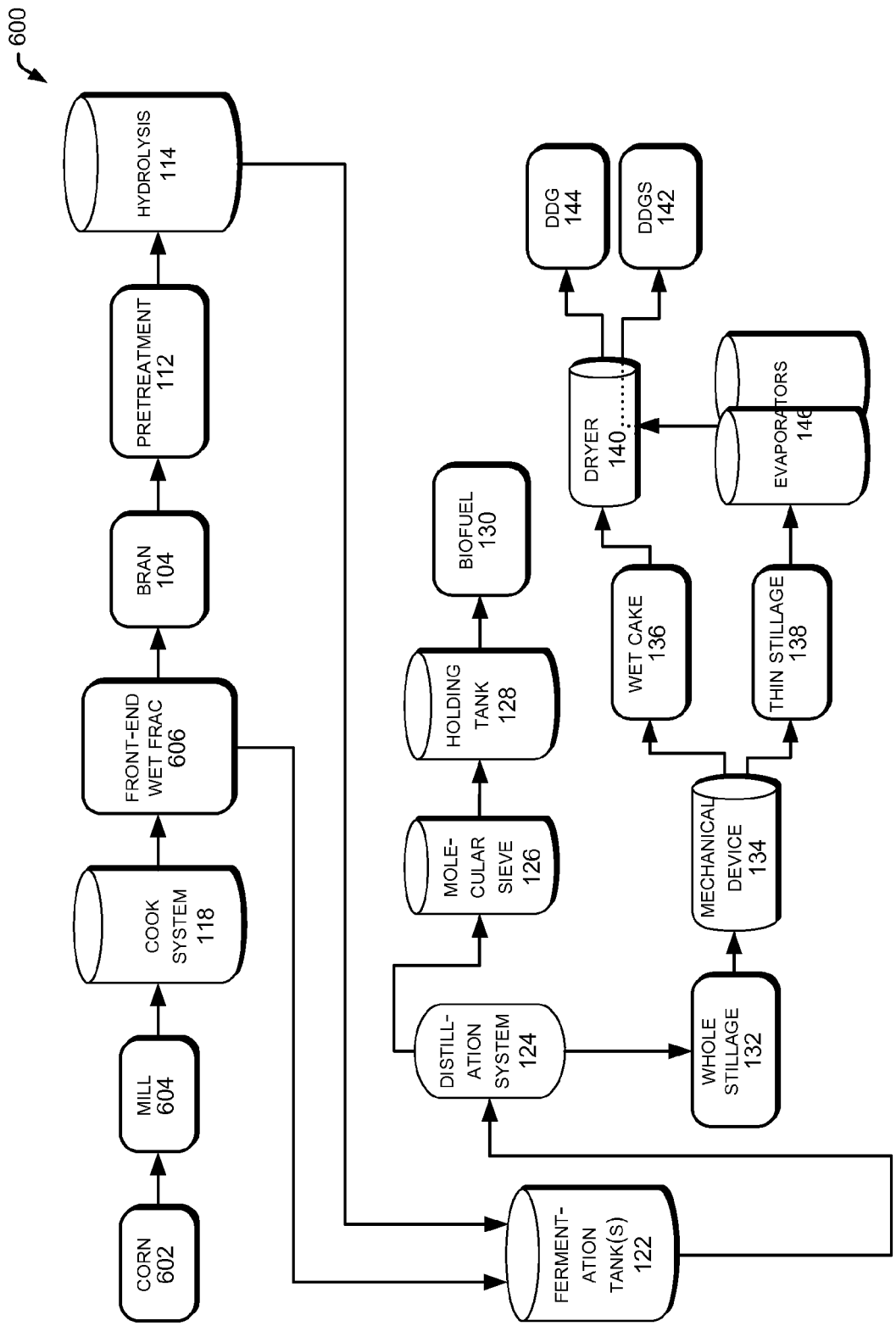
FIG. 6 illustrates an example process with front-end wet fractionation to produce cellulosic biofuel and high-value protein animal feed.

FIG. 6 illustrates an example process 600 with front-end wet fractionation to produce cellulosic biofuel, ethanol, and high-value protein animal feed. The processes in FIG. 6 that are similar to the processes in FIG. 1 will not be described again. FIG. 6 is similar to FIG. 1, except this figure illustrates another embodiment of the integrating processes with the existing facility that uses milling and front-end wet fractionation. Details of front-end wet fractionation 606 will be discussed in detail with reference to FIGS. 7, 8, and 9.

Prior to milling, the process 600 cleans the corn 602 by going through a grader. The grader may be an oscillatory screening device that separates items found with the corn 602. The separation occurs based on particle sizes. For instance, the process 600 screens large-size particles that may include trash or form materials, medium-size particles that include the corn 602, and small-size particles that may include sand, broken grains, and the like.

The process 600 sends the corn 602 to a bin hopper or a roll feeder and mills 604 the corn. Devices to mill 604 the corn 602 include but are not limited to, a hammer mill, roller mill, disc mill, ball mill, pin mill, a shaker table, an aspiration system, and the like. In an embodiment, two rolls may rotate at the same speed causing compression force to be used on the corn 602. In another embodiment, the two rolls may operate at different speeds to increase compression and shear stress. The roller mill may include screens that are located along the bottom of the rolls to allow particles of a certain size to pass through the screen.

The process 600 mills 604 the large-size particles from the separated streams, mixes the large-size particles from the separated streams in cook 118, adds enzymes, and cooks the slurry. The process 600 may receive the slurry from cook 118, which includes the slurry tank 116 and/or from the liquefaction tank 120. The process 600 further separates the different size particles in front-end wet fractionation 606 to separate out the bran 104 from the endosperm 106 and the germ 108. The rest of the processes shown in FIG. 6 are similar to the processes that were discussed with reference to FIG. 1.

Front-End Wet Fractionation Examples

Figure 7:
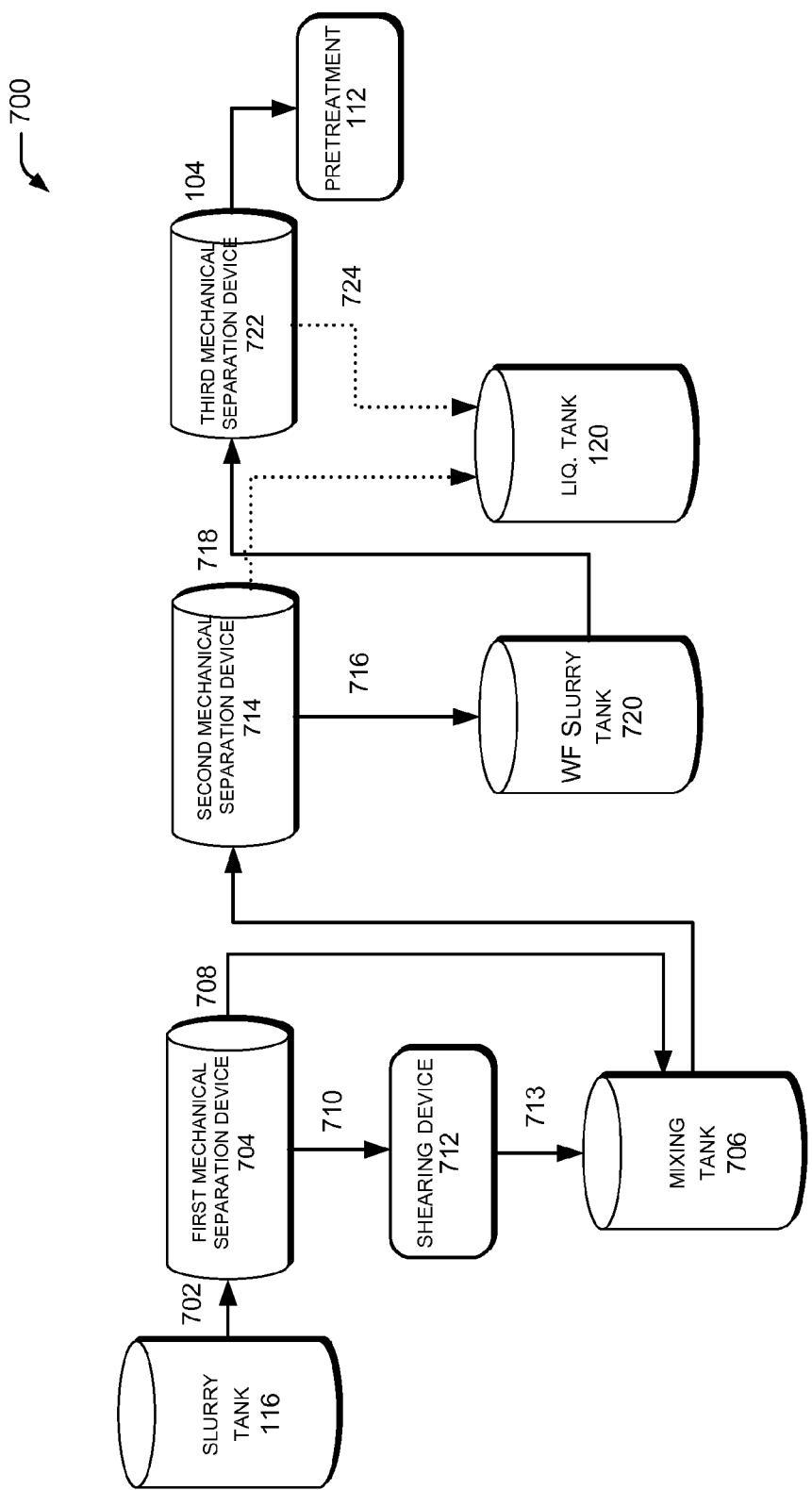
FIG. 7 illustrates an example process of the front-end wet fractionation.
Figure 8:
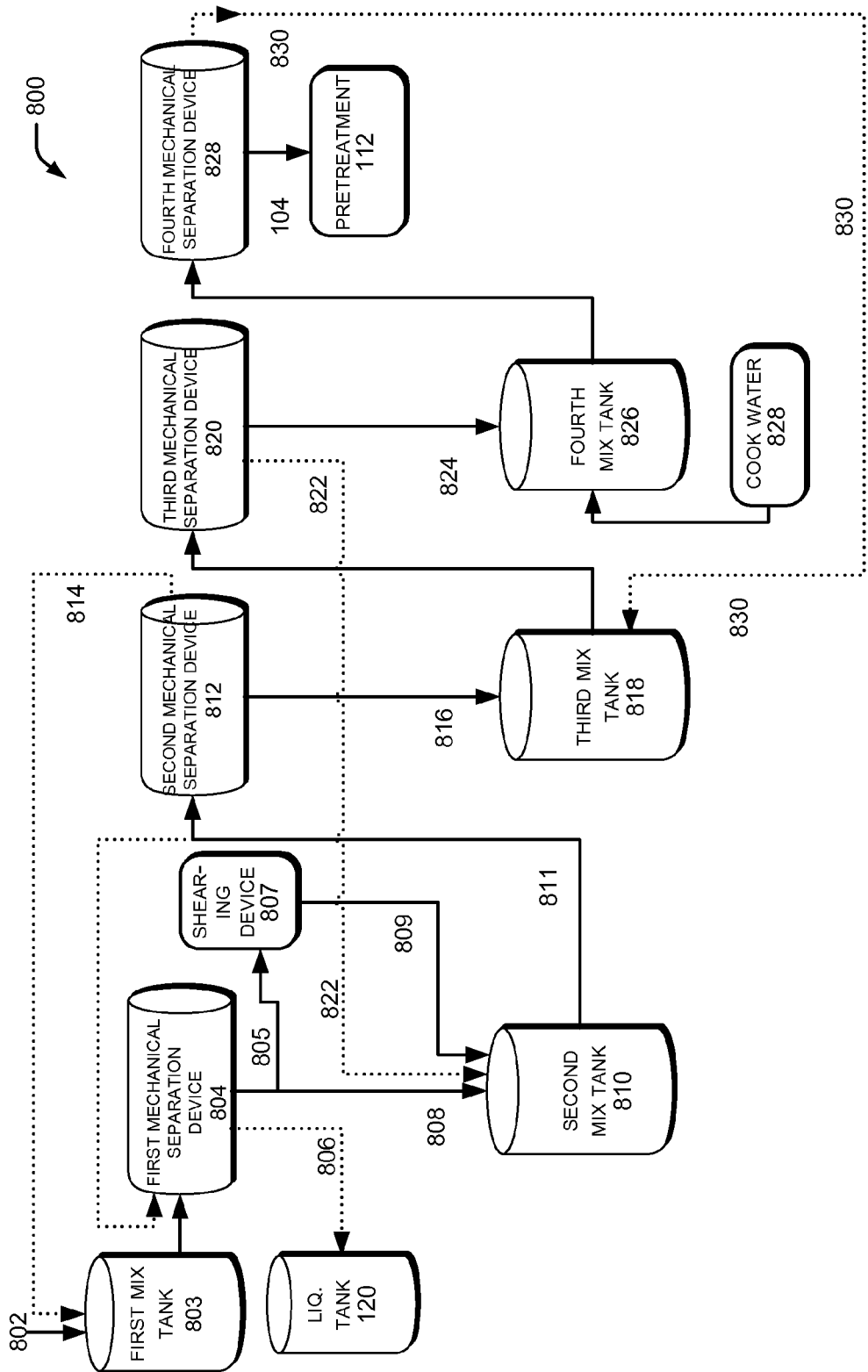
FIG. 8 illustrates another example process of the front-end wet fractionation.
Figure 9:
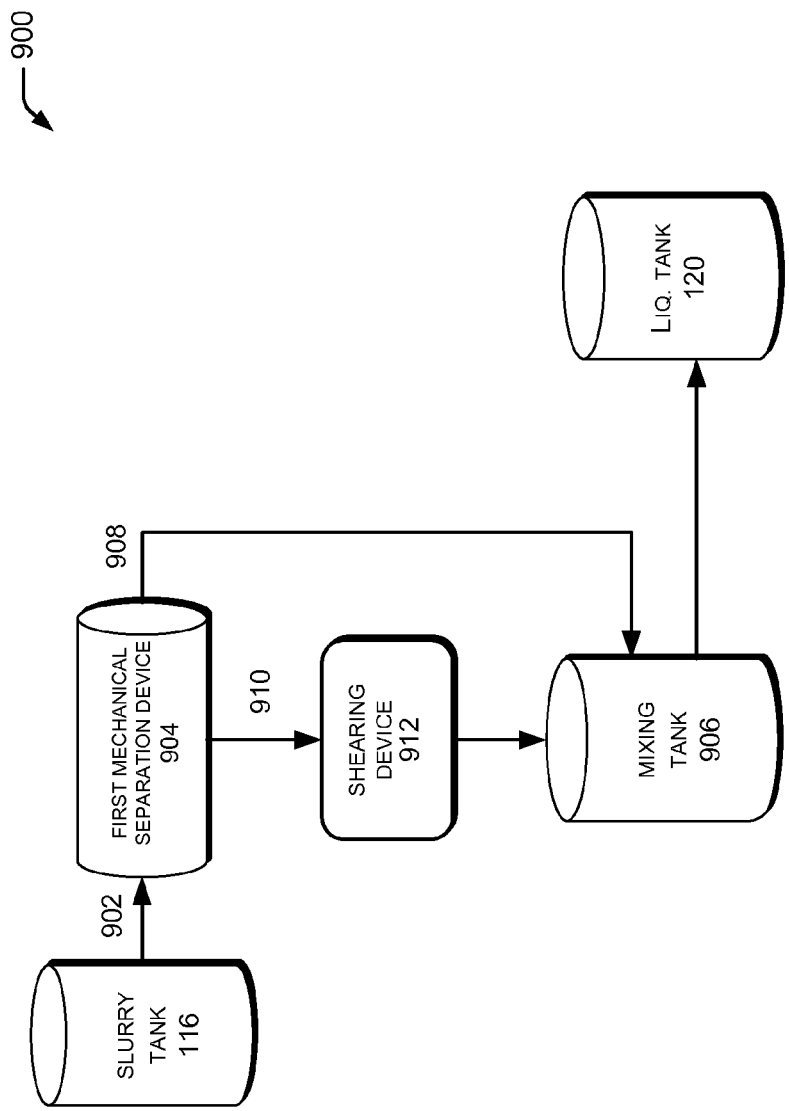
FIG. 9 illustrates another example process of the front-end wet fractionation.

FIGS. 7-9 illustrate examples of front-end wet fractionation to be used with the integrated process. The front-end wet fractionation process provides better separation of bran 104, endosperm 106, and germ 108 so the bran 104 may be pretreated and hydrolyzed. The front-end wet fractionation process enhances yield through starch liberation technology by providing an increase in yield of about 2% to 3%. The front-end wet fractionation process increases the starch surface area and provides starch accessibility to enzymes. Furthermore, the fermenting of the additional starch by the front-end wet fractionation process removes load from centrifuges, evaporators, and dryers in the existing facility.

For illustrative purposes, the liquids and fine suspended particles streams are identified by dotted lines to indicate being sent to tanks. These examples illustrate streams that may be received into tanks from identified mechanical separation devices. However, any streams may be received into the tanks from any of the mechanical separation devices.

FIG. 7 illustrates an example of a front-end wet fractionation (FEWF) 700 used with the integrated process. The process 700 receives a process stream 702, which may be a slurry from the slurry tank 116 prior to being cooked or mash from the liquefaction tank 120. The process 700 separates the components, and further washes the material. The process 700 sends the process stream 702 through a first mechanical separation device 704, which separates components such as the larger solid particles from the smaller particles and liquids stream.

The first mechanical separation device 704 may include paddles that rotate, a stationary drum, and an outer wall configured as a screen. The first mechanical separation device 704 pushes the process stream 702 against a perforated screen where the liquids and small particles 708 (i.e., starch, gluten, protein, salt, and the like) pass through the perforated screen and are sent to mixing tank 706. The paddles rotate to move the process stream 702 toward the perforated screen. The perforated screen has openings that are sized to allow water, starch, and smaller sized particles to flow through the perforated screen but will not allow the larger particles 710, such as fiber to flow through.

The process 700 produces the liquids and fine suspended particles stream 708 and a large suspended solids stream 710. The liquids and fine suspended particles stream 708 may include starch that has been washed and removed from the fiber. The process 700 sends the liquids and fine suspended particles stream 708 to the mixing tank 706.

The process 700 directs the large suspended solids stream 710 to a shearing device 712. The shearing device 712 may be a disc mill, roller mill, hammer mill, and the like to impart a high shear to the large suspended solids in the large suspended solids stream 710 without creating fines. The process 700 sends the milled large particles stream 713 to the mixing tank 706.

The stream in the mixing tank 706 may still contain starch and/or the food grade protein. Thus, the process 700 further sends the milled large particles stream 713 combined with the liquids and fine suspended particles stream 708 in the mixing tank 706 to a second mechanical separation device 714. The second mechanical separation device 714 separates components such as the larger solid particles stream 716 from the smaller particles and liquids stream 718. The process 700 sends the smaller particles and liquids stream 718 to the liquefaction tank 120 for further processing. While the process 700 sends the larger solid particles stream 716 to a wet fractionation tank, WF slurry tank 720. The process 700 further sends the larger solid particles stream 716 in the WF slurry tank 720 to a third mechanical separation device 722.

The third mechanical separation device 722 separates the fiber (i.e., bran 104) from the small particles and liquids stream, which is sent to pretreatment 112. The small particles and liquids stream 724 will be sent to a liquefaction tank 120.

The mechanical separation device includes at least one of a paddle machine, a washing paddle machine, a filtration centrifuge, a pressure DSM screen, or a gravity DSM screen. In an embodiment, the mechanical separation device is a paddle machine separation device having at least four rotating paddles with a stationary drum and an outer wall configured as a screen. In other embodiments, the paddle machine separation device may include at least two rotating paddles up to 20 rotating paddles.

FIG. 8 illustrates another example of the front-end wet fractionation (FEWF) 800 to be used with the integrated process. The process 800 receives a process stream 802, which may be a slurry from the slurry tank 116 or mash from the liquefaction tank 120 into a first mix tank 803. The process 800 sends the process stream 802 through the first mechanical separation device 804, which produces a liquids and fine suspended particles stream 806 and a large suspended solids stream 808. The process 800 sends the liquids and fine suspended particles stream 806 to the liquefaction tank 120.

A portion 805 of the large suspended solids stream 808 is directed towards a shearing device 807, which grinds the large suspended solids to become a milled solids stream 809. The process 800 sends the milled solids stream 809 to a second mix tank 810. Meanwhile, the process 800 sends the other portion of the large suspended solids stream 808 to the second mix tank 810. The second mix tank 810 also receives another liquids and fine suspended particles stream 822 (shown in dotted lines) from a third mechanical separation device 820. Here, the combined streams are mixed and heated to about 76° C. to about 85° C. (170° F. to about 185° F.) for about 1 to about 30 minutes. The process 800 sends this combined stream 811 from the second mix tank 810 to a second mechanical separation device 812. A portion of this combined stream 811 may be recycled back to the first mechanical separation device 804 (shown in dotted line).

The second mechanical separation device 812 washes and removes the starch from the fiber, producing another liquids and fine suspended particles stream 814 to be sent to the first mix tank 803 or alternatively, to makeup water for slurry tank 116 and another large suspended solids stream 816 to be sent to a third mix tank 818. Here, the combined streams are mixed and heated to about 76° C. to about 85° C. (170° F. to about 185° F.) for about 1 to about 30 minutes. The process 800 further sends this combined stream from the third mix tank 818 to a third mechanical separation device 820.

The third mechanical separation device 820 removes any starch left on the fiber, producing the another liquids and fine suspended particles stream 822 sent to the second mix tank 810 and another large suspended solids stream 824 to be sent to a fourth mix tank 826. Also, the fourth mix tank 826 receives cook water 828 from the existing facility. The cook water 828 being added to the large suspended stream 824 may create a lower-solids stream in the fourth mix tank 826. The cook water 828 may include but is not limited to hot dilution water. The cook water 828 may range from a temperature of about 75° C. to about 95° C. Here, the combined streams are mixed and heated in the fourth mix tank 826 to about 76° C. to about 85° C. (170° F. to about 185° F.) for about 1 to about 30 minutes.

The process 800 sends the stream from the fourth mix tank 826 to a fourth mechanical separation device 828. The fourth mechanical separation device 828 separates the fiber, bran 104 to be sent to pretreatment 112 and the liquids and fine suspended particles stream 830 to be sent to the third mix tank 818. (shown in dotted line).

The mechanical separation device includes at least one of a paddle machine, a washing paddle machine, a filtration centrifuge, a pressure DSM screen, or a gravity DSM screen. In an embodiment, the first mechanical separation device is a paddle machine separation device having at least four rotating paddles with a stationary drum and an outer wall configured as a screen. In other embodiments, the paddle machine separation device may include at least two rotating paddles up to 20 rotating paddles.

The washing paddle machine may include multiple stages of washing. For instance, there may be a two stage washing in the first mechanical separation device in an embodiment. However, any number of washings may be used, such as two, three, or four. The washing of the fiber or large solids helps to wash the starch and gluten or protein away from the fiber. The washing is countercurrent flow.

The first mix tank 803, the second mix tank 810, the third mix tank 818, and the fourth mix tank 826 may be a cook tank or any type of tank that includes an agitator. The residence time in the tanks may be predetermined based on variables. The variables may include size of the tank, amount of material, type of grain, and the like.

The cooking of the large suspended solids stream with the water causes the starch granules to absorb the water as heated. Thus, water is absorbed inside the granule. This swelling of the granule allows for improved enzyme action when returned to the start of the slurry process.

FIG. 9 illustrates another example of a front-end wet fractionation 900 used with the integrated process. The process 900 receives a process stream 902, which may be a slurry from the slurry tank 116 prior to being cooked or mash from the liquefaction tank 120. The process 900 separates the components, and further washes the material. The process 900 sends the process stream 902 through a first mechanical separation device 904, which separates components such as the larger solid particles from the smaller particles and liquids stream.

The first mechanical separation device 904 may include paddles that rotate, a stationary drum, and an outer wall configured as a screen. The first mechanical separation device 904 pushes the process stream 902 against a perforated screen where the liquids and small particles (i.e., starch, gluten, protein, salt, and the like) pass through the perforated screen and sent to mixing tank 906. The paddles rotate to move the process stream 902 toward the perforated screen. The perforated screen has openings that are sized to allow water, starch, and smaller sized particles to flow through the perforated screen but will not allow the larger particles, such as fiber to flow through.

The process 900 produces a liquids and fine suspended particles stream 908 and a large suspended solids stream 910. The liquids and fine suspended particles stream 908 may include starch that has been washed and removed from the fiber. The process 900 sends the liquids and fine suspended particles stream 908 to the mixing tank 906. The process 900 directs the large suspended solids stream 910 to a shearing device 912, which shears the large solids or particles.

In another embodiment, a mechanical separation device, such as a centrifuge or a paddle machine may receive the stream from the mixing tank to separate out the fiber and to send the liquids and fine suspended particles stream to the liquefaction tank 120.

Cellulosic Process with Back-End Wet Fractionation

Figure 10:
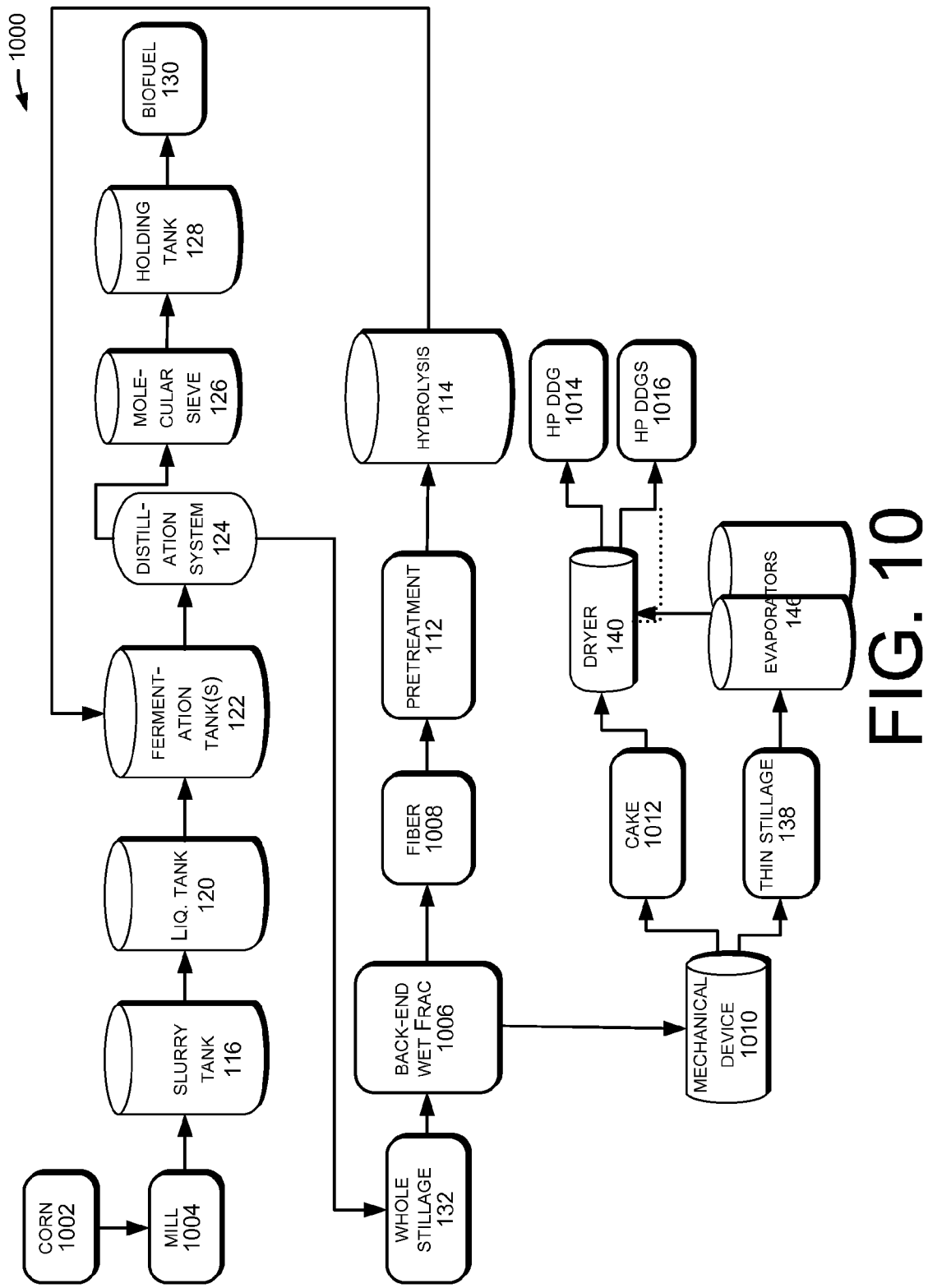
FIG. 10 illustrates an example process with back-end wet fractionation to produce cellulosic biofuel and high-value protein animal feed.

FIG. 10 illustrates an example process 1000 with back-end wet fractionation to produce cellulosic biofuel, ethanol, and high-value protein animal feed. The processes in FIG. 10 that are similar to the processes in FIG. 1 will not be described again. FIG. 10 is similar to FIG. 1, except this figure illustrates another embodiment of the integrating processes with the existing facility that uses milling and back-end wet fractionation. Details of back-end wet fractionation 1006 will be discussed in detail with reference to FIG. 11.

Prior to milling, the process 1000 cleans the corn 1002 by going through a grader. The grader may be an oscillatory screening device that separates items found with the corn 1002. The separation occurs based on particle sizes. For instance, the process 1000 screens large-size particles that may include trash or form materials, medium-size particles that include the corn 1002, and small-size particles that may include sand, broken grains, and the like.

The process 1000 sends the corn 1002 to a bin hopper or a roll feeder and mills 1004 the corn. Devices to mill 1004 the corn 1002 include but are not limited to, a hammer mill, roller mill, disc mill, ball mill, pin mill, a shaker table, an aspiration system, and the like.

The process 1000 produces whole stillage 132 from the distillation system 124. The whole stillage 132 is further separated in back-end wet fractionation 1006 to separate out the fiber 1008 from the other components in whole stillage 132.

Returning to 1006, the other components are directed to the mechanical device 1010. The mechanical device 1010 may be any type of separation device including, but not limited to, centrifuge, filter, paddle screen, screen, and the like. The mechanical device 1010 produces a cake 1012. The process 1000 may transfer some of the cake 1012 to one or more dryer(s) 140 to remove moisture. This drying produces high-protein (HP) animal feed, High Protein Dried Distillers Grain (HP DDG) 1014, which may be stored in tanks (not shown). Liquid that has been separated and concentrated is syrup. The dried syrup is added back into the HP DDG 1014 to create High Protein Dried Distillers Grain with Solubles (HP DDGS) 1016. The products have almost an indefinite shelf life and may be shipped to any market for feed to livestock. The rest of the processes shown in FIG. 10 is similar to the processes that were discussed with reference to FIG. 1.

Back-End Wet Fractionation

Figure 11:
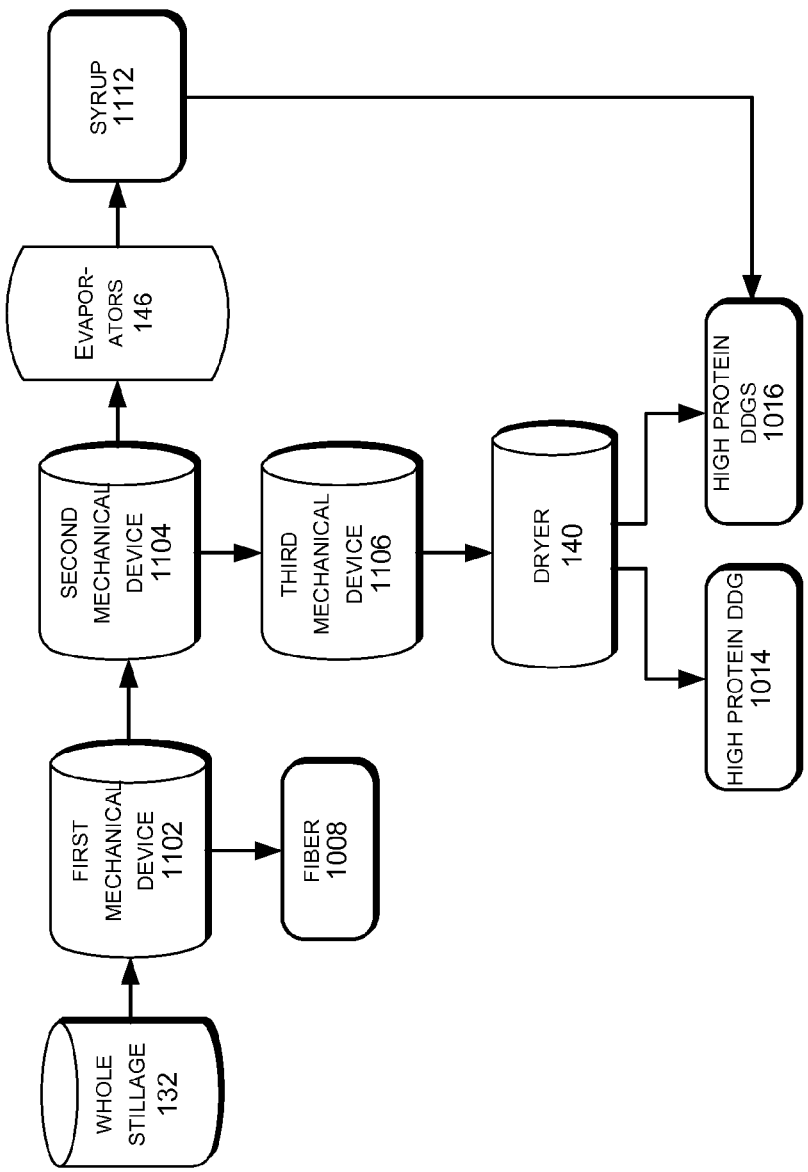
FIG. 11 illustrates an example process of the back-end wet fractionation.

FIG. 11 illustrates an example of a back-end wet fractionation 1006 in the integrated process. The process 1006 provides better separation of the fiber 1008, and other components so the fiber 1008 may be pretreated and hydrolyzed. It enhances yield through starch liberation technology by providing an increase in yield of 2% to 3%. The process 1006 increases the starch surface area and provides starch accessibility to enzymes. Furthermore, the fermenting of the additional starch by this process removes load from centrifuge, dryers, and evaporators in the existing facility.

The process 1006 separates the whole stillage 132 with a first mechanical device 1102 to produce two products. The first mechanical device 1102 separates out the fiber 1008 from the whole stillage stream. Next, the process 1006 sends the whole stillage stream through a second mechanical device 1104 to generate a first stream to the evaporators 146 and to dry out the first stream to create syrup 1112.

Returning to 1104, the process 1006 sends a second stream through a third mechanical device 1106. The process 906 further sends the second stream to a dryer 140, which dries the solids stream to produce a high protein high protein DDG 1014 and DDGS 1016 combined with syrup 1112.

The mechanical device may include, but is not limited to, a centrifuge, nozzle centrifuge, filtration centrifuge, decanter centrifuge, tricanter, and the like.

Examples of Results

The examples below are only representative of some aspects of this disclosure. It will be understood by those skilled in the art that processes as set forth in the specification can be practiced with a variety of alterations with the benefit of the disclosure. These examples and the procedures used therein should not be interpreted as limiting the invention in any way not explicitly stated in the claims.

Pretreatment Example

The pretreatment 112 was conducted in five discrete timeframes using sulfuric acid, ammonia, a mixed base of potassium hydroxide and sodium hydroxide, potassium hydroxide, and sodium hydroxide. Table I. summarizes the pretreatment runs below.

TABLE I

Pretreatment Runs

| Elapsed time hrs | Dry tons/day | % solids w/w | Acid % w/w as 100% H2SO4/ dry ton | Ammonia %w/w as anhydrous NH3/ dry ton | Mixed base % w/w as mixture of KOH (22.25%) NaOH (25%) | KOH use %w/w as 100% KOH/ dry ton | NaOH % w/w as 100% NaOH/ dry ton | Average temperature F. |
|---|---|---|---|---|---|---|---|---|
| 86-292 | 11.32 | 16.11% | 4.07% | 1.19% | NR | NR | NR | 311.09 |
| 337-437 | 11.35 | 16.07% | 3.83% | 1.09% | 3.43% | 0.76% | 0.86% | 311.00 |
| 456-698 | 11.37 | 16.39% | 3.83% | 1.08% | 3.90% | 0.87% | 0.98% | 312.15 |

TABLE I-continued

Pretreatment Runs

| Elapsed time hrs | Dry tons/day | % solids w/w | Acid % w/w as 100% H2SO4/ dry ton | Ammonia %w/w as anhydrous NH3/ dry ton | Mixed base % w/w as mixture of KOH (22.25%) NaOH (25%) | KOH use %w/w as 100% KOH/ dry ton | NaOH % w/w as 100% NaOH/ dry ton | Average temperature F. |
|---|---|---|---|---|---|---|---|---|
| 738-881 | 11.09 | 16.33% | 3.89% | 1.16% | 3.75% | 0.83% | 0.94% | 312.08 |
| 934-1214 | 10.59 | 15.41% | 3.87% | 1.10% | 2.34% | 0.52% | 0.58% | 310.08 |

NR Not Reporter: began reading at 367 hours but used average for entire time calculation of 337-437
Times during this portion of run when mixed base was off and ammonia added elsewhere for production of sugars for other collaborators.
Blend of ½ NaOH (50%) and % KOH (45%) by volume The pretreatment data indicate the percentages of solids ranged from 15.41% to 16.39%, the amount of sulfuric acid applied ranged from 3.83% to 4.07%, the amount of ammonia ranged from 1.08% to 1.19%, a mixed base of potassium hydroxide and sodium hydroxide ranged from 2.34% to 3.90%, the amount of potassium hydroxide ranged 0.52% to 0.87%, the amount of sodium hydroxide ranged from 0.58% to 098%, and the average temperature ranged from 310.08° F. to 312.08° F.

Pretreatment quality during the run remained relatively consistent with respect to hemicellulose conversion. There were relatively consistent concentrations of xylose, furfural, acetic acid and arabinose observed throughout the runs. Starch conversion to monomeric glucose increased gradually during the run. A steady increase in monomeric glucose and a steady decline in DP4+ peak indicate that oligomeric starches created in pretreatment are broken down to glucose more efficiently as run time elapsed. The starch content in the feedstock increased steadily during the run.

Hydrolysis Example

Hydrolysis 114 was conducted by generating 570,000 gallons of hydrolysate. The hydrolysis 114 included hydrolyzing 18 discrete batches of pretreated bran. Hydrolysis 114 converted the cellulose and hemicelluose to C6 (i.e., glucose) and C5 (i.e., xylose) sugars or monomeric components. The percentage of conversions for each batch and an average percent for glucose and xylose are shown in Table II.

TABLE II

Hydrolysis Conversion Data

| Batch | % TS | % C6 conv | % Xylose conv |
|---|---|---|---|
| 601 | 15.3 | 97.1 | 89.7 |
| 602 | 16.2 | 90.4 | 79.2 |
| 603 | 16.7 | 89.2 | 72.2 |
| 604 | 16.6 | 98.4 | 72.1 |
| 605 | 16.3 | 88.4 | 69.1 |
| 606 | 16.2 | 98.4 | 76.1 |
| 607 | 16.2 | 103.8 | 79.6 |
| 608 | 16.1 | 77.3 | 71.5 |
| 609 | 16.0 | 87.1 | 73.2 |
| 610 | 15.7 | 97.2 | 86.9 |
| 611 | 15.6 | 85.0 | 82.5 |
| 612 | 16.0 | 89.8 | 82.4 |
| 613 | 14.8 | 103.7 | 80.7 |
| 614 | 15.0 | 88.6 | 87.2 |
| 615 | 15.3 | 80.4 | 77.4 |
| 616 | 15.5 | 98.7 | 96.9 |

TABLE II-continued

Hydrolysis Conversion Data

| Batch | % TS | % C6 conv | % Xylose conv |
|---|---|---|---|
| 617 | 15.1 | 82.2 | 85.3 |
| 618 | 14.6 | 74.1 | 75.0 |
|  | 15.7 | 90.5 | 79.8 |

Table II. illustrates the hydrolysis 114 produced hydrolysate with an average of 15.7% total solids. The average percent conversion of C6 (i.e., glucose) is 90.5% and the average percent conversion of xylose (i.e., xylose) is 79.8%. Hydrolysis produced over 90% conversion of the C6.

Hybrid Hydrolysis and Fermentation Example

HHF reactors were used to demonstrate conversion of both pentose and hexose sugars in the integrated process. During a 1,000 hour run, 8 HHF batches (~4000 gallons each) were completed. The HHF process is a two-phase process composed of an initial time period with the hydrolysate at normal hydrolysis conditions (128° F., pH controlled 4.8-5.0) followed by a reduction in temperature to normal fermentation conditions (90° F., pH controlled 4.8-5.0). The hydrolysis run and total time are shown in Table III. below.

TABLE III

HHF Data

| Batch number | Hydrolyzate % TS w/w | Corrected Final ethanol titer g/L | Hydrolysis time/ total HHF time (hrs) | % fermentation yield |
|---|---|---|---|---|
| 401 | 15.4 | 33.4 | 30/86 | 0.78 |
| 402[a] | 17.0 | 27.1 | 30/150 | 0.65 |
| 403 | 16.4 | 35.5 | 30/97 | 0.82 |
| 404 | 17.0 | 37.5 | 30/95 | 0.86 |
| 414 | 17.9 | 36.9 | 15/60 | 0.89 |
| 415 | 14.7 | 31.1 | 15/60 | 0.83 |
| 416 | 15.0 | 30.2 | 15/60 | 0.76 |
| 417 | 15.9 | 33.2 | 15/68 | 0.89 |
| Average | 16.2 | 33.1 |  | 0.81 |

Initially, the conversions were targeted for 120 hours total with 30 hours dedicated for hydrolysis. As shown by batch numbers 414, 415, 416, the HHF total time was reduced to 60 hours and 15 hours dedicated for hydrolysis for these batches. The data indicate the percent fermentation yield was not affected by reducing the time in half. This is possible by doubling the yeast inoculum amount and enzyme dose.

Hydrolysis Methods and Variables

Different types of hydrolysis methods were run with different variable conditions. One method is separate hydrolysis of corn bran mixed with high solids corn mash (SHF-CM). This method tested the yield increase associated with fermenting the cellulose/starch mixed mash with standard non-GMO yeast (NABC-Bioferm).

Another method is corn bran hybrid hydrolysis and fermentation (HHF) beer mixed with high solids corn mash (HHF-CM). The pretreated corn bran slurry was hydrolyzed at 128° F. for 15-30 hours. The temperature was then dropped to 89° F. and a GMO yeast was added to the fermentation tanks to convert the five and six carbon sugars (not including arabinose) to a low titer beer (35-45 g/L). This beer was then mixed with the high solids corn mash.

Another method used high solids corn mash mixed with a volume of water equivalent to additions of corn bran hydrolysate or HHF beer (Water-CM). This test served as a control. The controlling factor was that all 4 batches received exactly the same amount of corn mash with exactly the same composition.

TABLE IV

Integrated Fermentation Data
(HHF-CM, SHF-CM, and Water-CM)

| Batch number | Type | Finish time | % yield Increase |
|---|---|---|---|
| 501 | SHF-CM | 54 | 6.5% |
| 502 | HHF-CM | 54 | 11.6% |
| 503 | HHF-CM | 54 | 11.2% |
| 504 | Water-CM | 54 | |
| 505 | SHF-CM | 54 | 7.3% |
| 506 | HHF-CM | 54 | 8.8% |
| 507 | HHF-CM | 54 | 8.7% |
| 508 | Water-CM | 54 | |
| 509 | SHF-CM | 60 | 7.4% |
| 510 | HHF-CM | 60 | 10.4% |
| 511 | HHF-CM | 60 | 8.8% |
| 512 | Water-CM | 60 | |
| 513 | SHF-CM | 60 | 8.5% |
| 514 | HHF-CM | 60 | 11.1% |
| 515 | HHF-CM | 60 | 11.1% |
| 516 | Water-CM | 60 | |
| 517 | SHF-CM | 60 | 6.2% |
| 518 | HHF-CM | 60 | 8.3% |
| 519 | HHF-CM | 60 | 8.2% |
| 520 | Water-CM | 60 | |
| 521 | SHF-CM | 60 | 6.5% |
| 522 | HHF-CM | 60 | 9.6% |
| 523 | HHF-CM | 60 | 9.1% |
| 524 | Water-CM | 60 | |
| average | SHF-CM | 58 | 7.1% |
| average | HHF-CM | 58 | 6.7% |
| average | Water-CM | 58 | |

The HHF-CM, batches 502, 503, 510, 514, and 515 showed % yield increases of 11.6%, 11.2%, 10.4%, 11.1%, and 11.1%, respectively. These yield increases are higher than the yield increases of the SHF-CM batches. Overall, the HHF-CM performed better than the SHF-CM and the control.

Integrated Fermentation Example

The three different methods included separate hydrolysis of corn bran mixed with high solids corn mash (SHF-CM), corn bran hybrid hydrolysis and fermentation (HHF) beer mixed with high solids corn mash (HHF-CM), and high solids corn mash mixed with a volume of water equivalent to additions of corn bran hydrolysate or HHF beer.

TABLE V

Integrated Fermentation Data

| Batch number | Type | Finish time | % yield Increase |
|---|---|---|---|
| 501 | SHF-CM | 54 | 6.5% |
| 502 | HHF-CM | 54 | 11.6% |
| 503 | HHF-CM | 54 | 11.2% |
| 504 | Water-CM | 54 | |
| 505 | SHF-CM | 54 | 7.3% |
| 506 | HHF-CM | 54 | 8.8% |
| 507 | HHF-CM | 54 | 8.7% |
| 508 | Water-CM | 54 | |
| 509 | SHF-CM | 60 | 7.4% |
| 510 | HHF-CM | 60 | 10.4% |
| 511 | HHF-CM | 60 | 8.8% |
| 512 | Water-CM | 60 | |
| 513 | SHF-CM | 60 | 8.5% |
| 514 | HHF-CM | 60 | 11.1% |
| 515 | HHF-CM | 60 | 11.1% |
| 516 | Water-CM | 60 | |
| 517 | SHF-CM | 60 | 6.2% |
| 518 | HHF-CM | 60 | 8.3% |
| 519 | HHF-CM | 60 | 8.2% |
| 520 | Water-CM | 60 | |
| 521 | SHF-CM | 60 | 6.5% |
| 522 | HHF-CM | 60 | 9.6% |
| 523 | HHF-CM | 60 | 9.1% |
| 524 | Water-CM | 60 | |
| average | SHF-CM | 58 | 7.1% |
| average | HHF-CM | 58 | 6.7% |
| average | Water-CM | 58 | |

Statistical evaluation of the ethanol titer data via HPLC analysis shows that the SHF-CM and HHF-CM produced 7.1% and 9.7% yield increases, respectively, when compared to the control. Additionally, these two different variable cases were found to be statistically different from each other.

All batches were completed in less than 60 hours. The HHF-CM batches showed an average percent yield increase of 9.7%, an average percent yeast reduction of 81.4% and an average percent glycerol reduction of 33%. Overall, the HHF-CM performed better than the SHF-CM and the control.

Although the subject matter has been described in language specific to structural features and/or methodological acts, it is to be understood that the subject matter defined in the appended claims is not necessarily limited to the specific features or acts described. Rather, the specific features and acts are disclosed as example forms of implementing the claims.

What is claimed is:

1. A method to treat corn feedstock in a dry grind process, the method comprising:
    sending the corn feedstock through a milling device; subsequently,
    forming a mash with the corn feedstock, the mash including a solids content between 18% and 40%; subsequently
    fractionating the mash by using a mechanical separation device by separating components of the mash into a first stream comprising bran and germ from a second stream comprising starch and protein;
    sending the first stream comprising the bran and the germ, which includes large suspended solids through a shearing device to impart shear on the large suspended solids;
    sending the second stream to a fermentation tank;
    pretreating the first stream comprising the bran and the germ by adding water to the first stream comprising the bran and the germ with the large, suspended solids in a tank to create a low-solids slurry, wherein a percentage of solids in the low-solids slurry comprises less than about 25%;

heating the low-solids slurry to increase temperature of the low-solids slurry to create a heated low-solids slurry;

adding a chemical to the heated low-solids slurry to cause a reaction zone to occur and to create a chemically treated low-solids slurry;

hydrolyzing and fermenting the chemically treated low-solids slurry to produce cellulosic beer using a cellulase enzyme complex cocktail in hydrolysis and an organism in fermentation;

sending the cellulosic beer to the fermentation tank; and fermenting the second stream and the cellulosic beer together in the fermentation tank.

2. The method of claim 1, wherein the water comprises at least one from an evaporator condensate, a pretreatment condensate, condensate from a flash tank, or condensate from side stripper bottoms.

3. The method of claim 1, wherein the increase in the temperature comprises ranging from about 355 K to about 478 K.

4. The method of claim 1, wherein the chemical comprises at least one of a sulfuric acid, a phosphoric acid, or a nitric acid.

5. The method of claim 1, wherein the hydrolyzing converts cellulose and hemicellulose to sugars in the low-solids slurry, at least 80% of the cellulose to glucose and converts at least 70% of the hemicellulose to monomeric components.

6. The method of claim 1, wherein the hydrolyzing and fermenting occurs in less than 60 hours.

7. The method of claim 1, further comprising adding a base in a flash tank, after the reaction zone to neutralize the low-solids slurry, wherein the base comprises at least one of anhydrous ammonia, sodium hydroxide, or potassium hydroxide.

8. The method of claim 1, further comprising: distilling the fermented cellulosic beer from the fermentation tank to separate alcohol from solids and liquids; removing moisture from the alcohol; and adding a denaturant to the alcohol to produce cellulosic biofuel.

9. The method of claim 1, wherein the mechanical separation device comprises at least one of a paddle machine, a washing paddle machine, a filtration centrifuge, a pressure DSM screen, or a gravity DSM screen.

10. The method of claim 1, wherein the mechanical separation device further comprises rotating and pushing the corn feedstock as a process stream against a screen.

11. The method of claim 1, wherein the milling device comprises at least a hammer mill.

12. The method of claim 1, wherein the shearing device comprises at least one of a disc mill or a roller mill.

13. The method of claim 1, wherein the cellulase enzyme complex cocktail comprises at least one of (i) a blend of cellulases, ⊖-glucosidases, and hemicellulase or (ii) a blend of cellulase of GH61 compounds, β-glucosidases, and hemicellulase.

14. The method of claim 1, wherein the organism comprises at least one of (i) a genetically modified organism metabolizing both 5-carbon and 6-carbon sugars, (ii) a metabolically engineered organism metabolizing both 5-carbon and 6-carbon sugars, (iii) a *Saccharomyces cerevisiae* yeast, or (iv) a genetically modified *Saccharomyces cerevisiae* yeast.

15. A method to treat corn in a process stream in a dry grind process, the method comprising:

milling the corn in the process stream through a milling device; subsequently, forming a mash with the corn, the mash including a solids content between 18% and 40%; subsequently fractionating the mash in the process stream in the mash with a mechanical separation device by separating components of the process stream into a first stream comprising fiber and germ from a second stream comprising starch and protein;

sending the second stream to a fermentation tank;

shearing the fiber and the germ from the first stream by going through a shearing device to impart shear on the fiber, and the germ;

pretreating the first stream comprising the fiber and the germ by adding water to the first stream comprising the fiber in a tank to create a low-solids slurry, wherein a percentage of solids in the low-solids slurry comprises less than about 25%;

heating the low-solids slurry to increase temperature of the low-solids slurry to create a heated low-solids slurry;

adding a chemical to the heated low-solids slurry to cause a reaction zone to occur to produce a chemically treated low-solids slurry;

hydrolyzing and fermenting the chemically treated low-solids slurry to produce cellulosic beer using a cellulase enzyme complex cocktail in hydrolysis and an organism in fermentation;

sending the cellulosic beer to the fermentation tank; and fermenting the second stream and the cellulosic beer together in the fermentation tank.

16. A method to treat corn feedstock, the method comprising:

treating the corn feedstock by milling the corn feedstock through a milling device; subsequently, forming a mash with the corn feedstock, the mash including a solids content between 18% and 40%; subsequently fractionating the mash with a mechanical separation device, comprising at least one of a paddle machine, a washing paddle machine, a filtration centrifuge, a pressure DSM screen, or a gravity DSM screen by separating components of the milled corn feedstock into a first stream comprising bran and germ from a second stream comprising starch and protein;

sending the second stream to a fermentation tank;

imparting shear on the first stream comprising the bran and the germ, wherein the shear imparted is on large, suspended solids;

pretreating the first stream comprising the bran and the germ by adding water to the first stream comprising the bran and the germ in a tank to create a low-solids slurry, wherein a percentage of solids in the low-solids slurry comprises less than about 25%;

heating the low-solids slurry to increase temperature of the low-solids slurry to produce a heated low-solids slurry;

adding a chemical to the heated low-solids slurry to cause a reaction zone to occur to produce a chemically treated low-solids slurry; and hydrolyzing and fermenting the chemically treated low-solids slurry to produce cellulosic beer using a cellulase enzyme complex cocktail in hydrolysis and an organism in fermentation;

sending the cellulosic beer to the fermentation tank; and fermenting the second stream and the cellulosic beer in the fermentation tank.

17. The method of claim 16, wherein the percentage of solids in the low-solids slurry is in a range of about 10-25%.

18. The method of claim 16, wherein the water comprises at least one of an evaporator condensate, a pretreatment condensate, condensate from a flash tank, or condensate from side stripper bottoms.

19. The method of claim 16, wherein the increase of temperate comprises ranging from about 355 K to 478 K.

20. The method of claim 16, wherein the chemical comprises at least one of a sulfuric acid, a phosphoric acid, or a nitric acid.

21. The method of claim 16, wherein the hydrolyzing converts cellulose and hemicellulose to sugars in the low-solids slurry, at least 80% of the cellulose to glucose and converts at least 70% of the hemicellulose to monomeric components.

22. A method to treat corn feedstock in a dry grind process, the method comprising:
   sending the corn feedstock through a milling device; subsequently,
   forming a mash with the corn feedstock, the mash including a solids content between 18% and 40%; subsequently
   fractionating the mash by using a mechanical separation device by separating components of the mash into a first stream comprising bran and germ from a second stream comprising starch and protein;
   sending the first stream comprising the bran and the germ, which includes large, suspended solids through a shearing device to impart shear on the large, suspended solids;
   sending the second stream to a fermentation tank;
   pretreating the bran by adding water to the bran in a tank to create a low-solids slurry, wherein a percentage of solids in the low-solids slurry comprises less than about 25%;
   heating the low-solids slurry to increase temperature of the low-solids slurry to create a heated low-solids slurry;
   adding a chemical to the heated low-solids slurry to cause a reaction zone to occur and to create a chemically treated low-solids slurry;
   hydrolyzing and fermenting the chemically treated low-solids slurry to produce cellulosic beer using a cellulase enzyme complex cocktail in hydrolysis and an organism in fermentation;
   sending the cellulosic beer to the fermentation tank;
   sending the germ to the fermentation tank; and
   fermenting the second stream, the germ, and the cellulosic beer together in the fermentation tank.

* * * * *